(12) United States Patent
Schalk

(10) Patent No.: US 9,969,999 B2
(45) Date of Patent: *May 15, 2018

(54) METHOD FOR PRODUCING ALPHA-SANTALENE

(71) Applicant: FIRMENICH SA, Geneva (CH)

(72) Inventor: Michel Schalk, Geneva (CH)

(73) Assignee: Firmenich SA, Geneva (CH)

( * ) Notice: Subject to any disclaimer, the term of this patent is extended or adjusted under 35 U.S.C. 154(b) by 28 days.

This patent is subject to a terminal disclaimer.

(21) Appl. No.: 15/060,060

(22) Filed: Mar. 3, 2016

(65) Prior Publication Data

US 2016/0177288 A1     Jun. 23, 2016

Related U.S. Application Data

(63) Continuation of application No. 12/918,140, filed as application No. PCT/EP2009/052546 on Mar. 4, 2009, now Pat. No. 9,297,004.

(30) Foreign Application Priority Data

Mar. 6, 2008 (EP) ..................... 08102357
Apr. 3, 2008 (EP) ..................... 08103362

(51) Int. Cl.
*C12N 9/88* (2006.01)
*C12P 5/00* (2006.01)
*C12P 15/00* (2006.01)

(52) U.S. Cl.
CPC ............... *C12N 9/88* (2013.01); *C12P 5/007* (2013.01); *C12P 15/00* (2013.01); *C12Y 402/03082* (2013.01)

(58) Field of Classification Search
CPC ....................................................... C12N 9/88
See application file for complete search history.

(56) References Cited

U.S. PATENT DOCUMENTS 9,297,004 B2 * 3/2016 Schalk ............... C12N 9/88

FOREIGN PATENT DOCUMENTS

| WO | 2004/031376 A2 | 4/2004 |
| WO | 2005/021705 A2 | 3/2005 |
| WO | 2006/134523 A2 | 12/2006 |
| WO | 2008/142318 A2 | 11/2008 |

OTHER PUBLICATIONS

Maruyama T., Ito M., Honda G.; "Molecular cloning, functional expression and characterization of (E)-beta farnesene synthase from Citrus junos."; Biol. Pharm. Bull. 24:1171-1175(2001).*
Zhao et al, Z. Naturforsch, 2004, 59c, 153-156.*
International Search Report and Written Opinion, Application No. PCT/EP2009/052546, dated May 15, 2009.
Altschul et al., "Basic Local Alignment Search Tool," J. Mol. Biol., 215:403-410 (1990).
Altschul, "Amino Acid Substitution Matrices from an Information Theoretic Perspective," J. Mol. Biol., 219:555-565 (1991).
Bouwmeester, "Engineering the essence of plants," Nature Biotechnology, 24(11):1359-1361 (Nov. 2006).
Chokeprasert et al., "Volatile components of the leaves, fruits and seeds of wampee [*Clausena lansium* (Lour.) Skeels]," Journal of Food Composition and Analysis, 20(1):52-56 (Feb. 2007).
Dewick, "The biosynthesis of C5-C25 terpenoid compounds," Nat. Prod. Rep., 19:181-222 (2002).
Keller et al., "Rapid synthesis of isoprenoid diphosphates and their isolation in one step using either thin layer or flash chromatography," Journal of Chromatography, 645:161-167 (1993).
Martin et al., "Engineering a mevalonate pathway in *Escherichia coli* for production of terpenoids," Nature Biotechnology, 21(7):796-802 (2003).
Maruyama et al., "Molecular Cloning, Functional Expression and Characterization of (E)-β-Farnesene Synthase from Citrus junos," Biol. Pharm. Bull., 24(10):1171-1175 (2001).
Pino et al., "Aromatic Plants from Western Cuba IV. Composition of the Leaf Oils of *Clausena lansium* (Lour.) Skeels and *Swinglea glutinosa* (Blanco) Meru," J. Essent. Oil Res., 18:139-141 (Mar./Apr. 2006).
Schardl et al., "Design and construction of a versatile system for the expression of foreign genes in plants," Gene, 61:1-11 (1987).
Stemmer, "DNA shuffling by random fragmentation and reassembly: In vitro recombination for molecular evolution," Proc. Natl. Acad. Sci. USA, 91:10747-10751 (Oct. 1994).
Takahashi et al., "Metabolic Engineering of Sesquiterpene Metabolism in Yeast," Biotechnology and Bioengineering, 37(1):170-181 (May 2007).
Tatusova et al., "Blast 2 Sequences, a new tool for comparing protein and nucleotide sequences," FEMS Microbiology Letters, 174:247-250 (1999).
van der Hoeven, "Genetic Control and Evolution of Sesquiterpene Biosynthesis in Lycopersicon esculentum and L. hirsutum," The Plant Cell, 12:2283-2294 (Nov. 2000).
Wu et al., "Redirection of cytosolic or plastidic isoprenoid precursors elevates terpene production in plants," Nature Biotechnology, 24(11):1141-1147 (Nov. 2006).
Zhao et al., "Chemical Composition of the Essential Oils of Clausena lansium from Hainan Island, China," Z Naturforsch C., 59:153-156 (2004).

(Continued)

*Primary Examiner* — Russell Kallis

(57) ABSTRACT

The present invention provides a method of producing α-santalene by contacting at least one polypeptide with farnesyl phyrophosphate (fpp). In particular, the method may be carried out in vitro or in vivo to produce α-santalene, a very useful compound in the fields of perfumery and flavoring. The present invention also provides the amino acid sequence of a polypeptide useful in the method of the invention. A nucleic acid encoding the polypeptide of the invention and an expression vector containing the nucleic acid represent part of the present invention. A non-human host organism and a cell transformed to be used in the method of producing α santalene are also part of the present invention.

22 Claims, 3 Drawing Sheets

(56) References Cited

OTHER PUBLICATIONS

U.S. Appl. No. 12/918,140, Restriction Requirement, dated Jan. 12, 2011.
U.S. Appl. No. 12/918,140, Non-Final Rejection, dated May 9, 2011.
U.S. Appl. No. 12/918,140, Final Rejection, dated Nov. 2, 2011.
U.S. Appl. No. 12/918,140, Advisory Action, dated Jan. 3, 2012.
U.S. Appl. No. 12/918,140, Non-Final Rejection, dated Aug. 12, 2014.
U.S. Appl. No. 12/918,140, Final Rejection, dated May 19, 2015.
U.S. Appl. No. 12/918,140, Notice of Allowance, dated Nov. 20, 2015.
U.S. Appl. No. 12/918,140, Corrected Notice of Allowability, dated Dec. 3, 2015.

* cited by examiner

Mass spectrum from the peak at retention time of 12.63 min

Mass spectrum of an alpha-santalene authentic standard

METHOD FOR PRODUCING ALPHA-SANTALENE

CROSS-REFERENCE TO RELATED APPLICATIONS

This application is a continuation of U.S. patent application Ser. No. 12/918,140 filed Aug. 18, 2010, which is a 371 filing of International patent application no. PCT/EP2009/052546 filed Mar. 4, 2009, which claims priority to European patent applications nos. 08103362.3 filed Apr. 3, 2008 and Ser. No. 08/102,357.4 filed Mar. 6, 2008. The entire contents of these applications are incorporated herein by reference thereto.

TECHNICAL FIELD

The present invention provides a method of producing α-santalene, said method comprising contacting at least one polypeptide with farnesyl pyrophosphate (FPP). In particular, said method may be carried out in vitro or in vivo to produce α-santalene, a very useful compound in the fields of perfumery and flavoring. The present invention also provides the amino acid sequence of a polypeptide useful in the method of the invention. A nucleic acid encoding the polypeptide of the invention and an expression vector containing said nucleic acid are also part of the present invention. A non-human host organism or a cell transformed to be used in the method of producing α-santalene is also an object of the present invention.

PRIOR ART

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Over 300 sesquiterpene hydrocarbons and 3000 sesquiterpenoids have been identified and many new structures are identified each year. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized. The biosynthesis of terpenes in plants and other organisms has been extensively studied and is not further detailed in here, but reference is made to Dewick, *Nat. Prod. Rep.*, 2002, 19, 181-222, which reviews the state of the art of terpene biosynthetic pathways.

α-santalene is a naturally occurring sesquiterpene molecule. The (+)-isomer can be used as starting material for the chemical synthesis or the biosynthesis of (Z)-(+)-α-santalol, which is an important constituent of sandalwood oil. Sandalwood oil is an important perfumery ingredient obtained by distillation of the heartwood of Santalum species. Sandalwood is also largely used for incenses and traditional medicine. The oil contains 90% of sesquiterpene alcohols. (Z)-(+)-α-santalol and (Z)-(-)-β-santalol represent the major constituents (respectively 45-47% and 20-30%) and are mainly responsible for the typical sweet-woody and balsamic odour of sandalwood oil. Other constituents such as epi-β-santalol and trans-α-bergamotol are also present and may contribute to the sandalwood note.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years. Due to over-exploitation of the natural resources, difficulties of cultivation, slow growth of the Santalum plants, the availabilities of sandalwood raw material has dramatically decreased during the past decades. Therefore, it would be an advantage to provide a source of (Z)-(+)-α-santalol, which is less subjected to fluctuations in availability and quality. A chemical synthesis of the sandalwood sesquiterpene constituents is so far not available. A biochemical pathway leading to the synthesis of (+)-α-santalene, which could then be used to produce (Z)-(+)-α-santalol, would therefore be of great interest. Given the difficulty to control sesquiterpene production in Santalum species, alternate plant sources were sought.

Santalane type sesquiterpene, and particularly sesquiterpenes with the α-santalane skeleton, were identified in several plant species. *Clausena lansium*, a plant from the Rutaceae family has been reported to contain large quantities of santalane sesquiterpenes in the leaves. Zhao and coworkers (Zhao et al, *Z. Naturforsch*, 2004, 59c, 153-156) have analyzed the leaves of *C. lansium* from China and detected the presence of α-santalol and β-santalol. The analysis of the leaves of *C. lansium* from Cuba, has revealed the presence of (Z)-α-santalol, epi-β-santalol, (Z)-β-santalol and (E)-β-santalol (Pino et al., *J. Essent. Oil Res.*, 2006, 18, 139-141). Surprisingly the analysis of different parts of *C. lansium* from Thailand origin did not show the presence of sesquiterpenes with santalane skeletons (Chokeprasert et al, *Journal of Food Composition and Analysis*, 2007, 20(1), 52-56).

A sesquiterpene synthase capable of synthesizing at least one bi-cyclic and/or tri-cyclic sesquiterpene having a santalane carbon skeleton, the corresponding nucleic acid and a method for producing such compounds having a santalane carbon skeleton are disclosed in the International patent application WO 2006/134523. (+)-epi-β-santalene, (-)-β-santalene, (+)-β-santalene, (+)-α-santalene and (-)-α-santalene are cited as examples of compounds having a santalane carbon skeleton. Nevertheless, the sesquiterpene synthase provided in the examples does not produce α-santalene. Only epi-β-santalene is produced. The properties of this compound are very different from those of α-santalene. In particular, epi-β-santalene is of no interest in the synthesis of (Z)-(+)-α-santalol. Moreover, the sesquiterpene synthase disclosed in WO 2006/134523 shares only 37% identity with the sequence of the invention.

Terpene synthases having a certain percentage of sequence identity with the sequence of the α-santalene synthase of the present invention have also been found in the sequences databases. Nevertheless, the percentage of identity between the known sesquiterpene synthases and the polypeptide of the invention is very low. The closest protein sequence to the (+)-α-santalene synthase of the invention is a (E)-β-farnesene synthase from Citrus junos (NCBI access No. AAK54279; Maruyama et al, *Biol. Pharm. Bull.*, 2001, 24(10), 1171-1175) which shares 67 to 68% amino acid sequence identity with the α-santalene synthase of the invention.

In addition to the difference between the sequences themselves, it also has to be pointed out that the structure and the properties of the products synthesized by the above-mentioned enzyme are very different from those of α-santalene. In particular (E)-β-farnesene is not suitable as a starting material for the synthesis of (Z)-(+)-α-santalol, which is a very useful ingredient in the field of perfumery.

An α-santalene synthase is disclosed in WO 2008/142318. This document was not published at the priority date of the present application. It describes an enzyme capable of catalyzing the transformation of Z,Z-farnesyl pyrophosphate to α-santalene. Therefore the reaction catalyzed by the prior art enzyme is different from the one catalyzed by the synthase of the present invention, which starts from E,E-farnesyl pyrophosphate. Moreover, the α-santalene synthase of the invention shares only 23.8% of sequence identity with the one described in WO 2008/142318.

Despite extensive studies of terpene cyclization, the isolation and characterization of the terpene synthases is still difficult, particularly in plants, due to their low abundance, their often transient expression patterns, and the complexity of purifying them from the mixtures of resins and phenolic compounds in tissues where they are expressed.

It is an objective of the present invention to provide methods for making (+)-α-santalene in an economic way, as indicated above. Accordingly, the present invention has the objective to produce (+)-α-santalene while having little waste, a more energy and resource efficient process and while reducing dependency on fossil fuels. It is a further objective to provide enzymes capable of synthesizing α-santalene, which is useful as perfumery and/or aroma ingredients.

| Abbreviations Used | |
|---|---|
| bp | base pair |
| kb | kilo base |
| BSA | bovine serum albumin |
| DMAPP | dimethylallyl diphosphate |
| DNA | deoxyribonucleic acid |
| cDNA | complementary DNA |
| dT | deoxy thymine |
| dNTP | deoxy nucleotide triphosphate |
| DTT | dithiothreitol |
| FPP | farnesyl pyrophosphate |
| GC | gaseous chromatograph |
| idi | isopentenyl diphosphate isomerase |
| IPP | isopentenyl diphosphate |
| IPTG | isopropyl-D-thiogalacto-pyranoside |
| LB | lysogeny broth |
| MOPSO | 3-(N-morpholino)-2-hydroxypropanesulfonic acid |
| MS | mass spectrometer |
| mvaK1 | mevalonate kinase |
| mvaK2 | mevalonate diphosphate kinase |
| NMR | nuclear magnetic resonance |
| PCR | polymerase chain reaction |
| RMCE | recombinase-mediated cassette exchange |
| 3'-/5'-RACE | 3' and 5' rapid amplification of cDNA ends |
| RNA | ribonucleic acid |
| mRNA | messenger ribonucleic acid |

DESCRIPTION OF THE INVENTION

The present invention provides a method to biosynthetically produce α-santalene in an economic, reliable and reproducible way.

A "sesquiterpene synthase" or a "polypeptide having a sesquiterpene synthase activity", is intended here as a polypeptide capable of catalyzing the synthesis of a sesquiterpene molecule or of a mixture of sesquiterpene molecules from the acyclic terpene precursor FPP.

As an "α-santalene synthase" or as a "polypeptide having an α-santalene synthase activity", we mean here a polypeptide capable of catalyzing the synthesis of α-santalene, in the form of any of its stereoisomers or a mixture thereof, starting from FPP. α-Santalene may be the only product or may be part of a mixture of sesquiterpenes.

As a "(+)-α-santalene synthase" or as a "polypeptide having a (+)-α-santalene synthase activity", we mean here a polypeptide capable of catalyzing the synthesis of (+)-α-santalene starting from FPP. (+)-α-santalene may be the only product or may be part of a mixture of sesquiterpenes. The (+)-α-santalene synthase is a particular example of α-santalene synthase.

The ability of a polypeptide to catalyze the synthesis of a particular sesquiterpene (for example (+)-α-santalene) can be simply confirmed by performing the enzyme assay as detailed in Example 4.

According to a preferred embodiment of the invention, FPP is in the form of (2E,6E)-FPP.

According to the present invention, polypeptides are also meant to include truncated polypeptides provided that they keep their sesquiterpene synthase activity as defined in any of the above embodiments and that they share at least the defined percentage of identity with the corresponding fragment of SEQ ID NO:1.

As intended herein below, "a nucleotide sequence obtained by modifying SEQ ID NO:2" encompasses any sequence that has been obtained by changing the sequence of SEQ ID NO:2 using any method known in the art, for example by introducing any type of mutations such as deletion, insertion or substitution mutations. Examples of such methods are cited in the part of the description relative to the variant polypeptides and the methods to prepare them.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.*, 1999, 174:247-250, 1999) set to the default parameters, available from the National Center for Biotechnology Information (NCBI) at http://www.ncbi.nlm.nih.gov/BLAST/bl2seq/wblast2.cgi, can be used to obtain an optimal alignment of peptidic or nucleotidic sequences and to calculate the percentage of sequence identity.

One object of the present invention is therefore a method for producing α-santalene comprising
a) contacting FPP with at least one polypeptide having an α-santalene synthase activity and comprising an amino acid sequence at least 50% identical to SEQ ID NO:1;
b) optionally, isolating the α-santalene produced in step a).

According to a preferred embodiment, the method is a method for producing α-santalene as a major product. According to an even more preferred embodiment, α-santalene represents at least 60%, preferably at least 80%, preferably at least 90%, preferably at least 92% of the product produced by the method of the invention.

According to a more preferred embodiment, the method is a method for producing (+)-α-santalene and the polypeptide having an α-santalene synthase activity has a (+)-α-santalene synthase activity.

According to an even more preferred embodiment, the method is a method for producing (+)-α-santalene as a major product. According to a most preferred embodiment, (+)-α-santalene represents at least 60%, preferably at least 80%, preferably at least 90%, preferably at least 92% of the products produced by the method of the invention.

The method can be carried out in vitro as well as in vivo, as will be explained in details further on.

The polypeptide to be contacted with FPP in vitro can be obtained by extraction from any organism expressing it, using standard protein or enzyme extraction technologies. If the host organism is a unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having an α-santalene synthase activity, either in an isolated form or together with other proteins, for example in a crude protein extract obtained from cultured cells or microorganisms, may then be suspended in a buffer solution at optimal pH. If adequate, salts, BSA and other kinds of enzymatic co-factors, may be added in order to optimize enzyme activity. Appropriate conditions are described in more details in the Examples further on.

The precursor FPP may then be added to the suspension or solution, which is then incubated at optimal temperature, for example between 15 and 40° C., preferably between 25 and 35° C., more preferably at 30° C. After incubation, the α-santalene produced may be isolated from the incubated solution by standard isolation procedures, such as solvent extraction and distillation, optionally after removal of polypeptides from the solution.

According to another preferred embodiment, the method of any of the above-described embodiments is carried out in vivo. In this case, step a) comprises cultivating a non-human host organism or cell capable of producing FPP and transformed to express at least one polypeptide comprising an amino acid sequence at least 50% identical to SEQ ID NO:1 and having an α-santalene synthase activity, under conditions conducive to the production of α-santalene.

According to a more preferred embodiment, the method further comprises, prior to step a), transforming a non human organism or cell capable of producing FPP with at least one nucleic acid encoding a polypeptide comprising an amino acid sequence at least 50% identical to SEQ ID NO:1 and having an α-santalene synthase activity, so that said organism expresses said polypeptide.

These embodiments of the invention are particularly advantageous since it is possible to carry out the method in vivo without previously isolating the polypeptide. The reaction occurs directly within the organism or cell transformed to express said polypeptide.

According to a particular embodiment of the invention, the at least one nucleic acid encoding the α-santalene synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to a more preferred embodiment, said nucleic acid comprises the nucleotide sequence SEQ ID NO:2 or the complement thereof. In an even more preferred embodiment, said nucleic acid consists of SEQ ID NO:2 or the complement thereof.

According to a more preferred embodiment the at least one nucleic acid used in any of the above embodiments comprises a nucleotide sequence that has been obtained by modifying SEQ ID NO:2. According to an even more preferred embodiment, said at least one nucleic acid consists of a nucleotide sequence that has been obtained by modifying SEQ ID NO:2.

According to another embodiment, the at least one nucleic acid is isolated from *Clausena lansium*.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications Martin, V. J., Pitera, D. J., Withers, S. T., Newman, J. D., and Keasling, J. D. *Nat Biotechnol.*, 2003, 21(7), 796-802 (transformation of *E. coli*); Wu, S., Schalk, M., Clark, A., Miles, R. B., Coates, R., and Chappell, J., *Nat Biotechnol.*, 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering*, 2007, 97(1), 170-181 (transformation of yeast).

To carry out the invention in vivo, the host organism or cell is cultivated under conditions conducive to the production of α-santalene. Accordingly, if the host is a transgenic plant, optimal growth conditions are provided, such as optimal light, water and nutrient conditions, for example. If the host is a unicellular organism, conditions conducive to the production of α-santalene may comprise addition of suitable cofactors to the culture medium of the host. In addition, a culture medium may be selected, so as to maximize α-santalene synthesis. Optimal culture conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or yeast. Most preferably, said bacteria is *E. coli* and said yeast is *Saccharomyces cerevisiae*.

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are preferably plant or fungal cells.

According to a preferred embodiment, the at least one polypeptide having an α-santalene synthase activity used in any of the above-described embodiments or encoded by the nucleic acid used in any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, said polypeptide comprises the amino acid sequence SEQ ID NO:1. In an even more preferred embodiment, said polypeptide consists of SEQ ID NO:1.

According to another preferred embodiment, the at least one polypeptide having an α-santalene synthase activity used in any of the above-described embodiments or encoded by the nucleic acid used in any of the above-described embodiments comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2. According to a more preferred embodiment, the at least one polypeptide having an α-santalene synthase activity used in any of the above-described embodiments or encoded by the nucleic acid used in any of the above-described embodiments consists of an amino acid sequence that is a variant of SEQ ID NO:1 obtained by genetic engineering, i.e. an amino acid sequence encoded by a nucleotide sequence that has been obtained by modifying SEQ ID NO:2.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

According to another embodiment, the at least one polypeptide having an α-santalene synthase activity used in any of the above-described embodiments or encoded by the nucleic acid used in any of the above-described embodiments is isolated from *Clausena lansium*.

An important tool to carry out the method of the invention is the polypeptide itself. A polypeptide having an α-santalene synthase activity and comprising an amino acid sequence at least 50% identical to SEQ ID NO:1 is therefore another object of the present invention.

According to a preferred embodiment, the polypeptide is capable of producing α-santalene as a major product. According to an even more preferred embodiment, it is capable of producing a mixture of sesquiterpenes wherein α-santalene represents at least 60%, preferably at least 80%, preferably at least 90%, preferably at least 92% of the sesquiterpenes produced.

According to a more preferred embodiment, the polypeptide has a (+)-α-santalene synthase activity.

According to an even more preferred embodiment, the polypeptide is capable of producing (+)-α-santalene as a major product. According to an even more preferred embodiment, it is capable of producing a mixture of sesquiterpenes wherein (+)-α-santalene represents at least 60%, preferably at least 80%, preferably at least 90%, preferably at least 92% of the sesquiterpenes produced.

According to a preferred embodiment, the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, the polypeptide comprises the amino acid sequence SEQ ID NO:1. According to an even more preferred embodiment, the polypeptide consists of SEQ ID NO:1.

According to another preferred embodiment, the at least one polypeptide comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2. According to a more preferred embodiment, the at least one polypeptide having an α-santalene synthase activity consists of an amino acid sequence that is a variant of SEQ ID NO:1 obtained by genetic engineering, i.e. an amino acid sequence encoded by a nucleotide sequence that has been obtained by modifying SEQ ID NO:2.

According to another embodiment, the polypeptide is isolated form *Clausena lansium*.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention.

As mentioned above, the nucleic acid encoding the polypeptide of the invention is a useful tool to modify non-human host organisms or cells intended to be used when the method is carried out in vivo.

A nucleic acid encoding a polypeptide according to any of the above-described embodiments is therefore also an object of the present invention.

According to a preferred embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to a more preferred embodiment, the nucleic acid comprises the nucleotide sequence SEQ ID NO:2 or the complement thereof. According to an even more preferred embodiment, the nucleic acid consists of SEQ ID NO:2 or the complement thereof According to another embodiment, the nucleic acid is isolated from *Clausena lansium*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

According to a more preferred embodiment, the at least one nucleic acid according to any of the above embodiments comprises a nucleotide sequence that has been obtained by modifying SEQ ID NO:2. Preferably said nucleic acid consists of a nucleotide sequence that has been obtained by modifying SEQ ID NO:2.

The nucleic acids comprising a sequence obtained by mutation of SEQ ID NO:2 or the complement thereof are encompassed by the invention, provided that the sequences they comprise share at least the defined percentage of identity with the corresponding fragments of SEQ ID NO:2 or with the complement thereof and provided that they encode a polypeptide having an α-santalene synthase activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having an α-santalene synthase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a preferred embodiment, the non-human host organism is a plant, a prokaryote or a fungus. Any plant, prokaryote or fungus is suitable to be transformed according to the present invention. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism is a microorganism. Any microorganism is suitable for the present invention, but according to an even more preferred embodiment said microorganism is a bacteria or yeast. Most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual,* 2$^{nd}$ edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In order to carry out the method for producing α-santalene in vitro, as exposed herein above, it is very advantageous to provide a method of making at least one polypeptide having an α-santalene synthase activity as described in any embodiment of the invention. Therefore, the invention provides a method for producing at least one polypeptide according to any embodiment of the invention comprising a) culturing a non-human host organism or cell transformed with the expression vector of the invention, so that it harbors a nucleic acid according to the invention and expresses or over-expresses a polypeptide of the invention;

b) isolating the polypeptide from the non-human host organism or cell cultured in step a).

According to a preferred embodiment, said method further comprises, prior to step a), transforming a non-human host organism or cell with the expression vector of the invention, so that it harbors a nucleic acid according to the invention and expresses or over-expresses the polypeptide of the invention.

A nucleic acid according to any of the above-described embodiments can be used.

Transforming and culturing of the non-human host organism or cell can be carried out as described above for the method of producing α-santalene in vivo. Step b) may be performed using any technique well known in the art to isolate a particular polypeptide from an organism or cell.

A "polypeptide variant" as referred to herein means a polypeptide having an α-santalene synthase activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry,* 1983, Addison-Wesley Pub. Co. The effects of such substitutions can be calculated using substitution score matrices such a PAM-120, PAM-200, and PAM-250 as discussed in Altschul, *J. Mol. Biol.,* 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptide encompassed by the invention also comprise fusion polypeptides resulting from a fusion of other functional proteins, such as other proteins from the terpene biosynthesis pathway.

Therefore, in an embodiment, the present invention provides a method for preparing a variant polypeptide having an α-santalene synthase activity, as described in any of the above embodiments, and comprising the steps of:
(a) selecting a nucleic acid according to any of the embodiments exposed above;
(b) modifying the selected nucleic acid to obtain at least one mutant nucleic acid;
(c) transforming host cells or unicellular organisms with the mutant nucleic acid sequence to express a polypeptide encoded by the mutant nucleic acid sequence;
(d) screening the polypeptide for at least one modified property; and,
(e) optionally, if the polypeptide has no desired variant α-santalene synthase activity, repeating the process steps (a) to (d) until a polypeptide with a desired variant α-santalene synthase activity is obtained;
(f) optionally, if a polypeptide having a desired variant α-santalene synthase activity was identified in step d), isolating the corresponding mutant nucleic acid obtained in step (c).

According to a preferred embodiment, the variant polypeptide prepared is capable of producing α-santalene as a major product. According to an even more preferred embodiment, it is capable of producing a mixture of sesquiterpenes wherein α-santalene represents at least 60%, preferably at least 80%, preferably at least 90%, preferably at least 92% of the sesquiterpenes produced.

According to a more preferred embodiment, the variant polypeptide prepared has a (+)-α-santalene synthase activity.

According to an even more preferred embodiment, the variant polypeptide prepared is capable of producing (+)-α-santalene as a major product. According to an even more preferred embodiment, it is capable of producing a mixture of sesquiterpenes wherein (+)-α-santalene represents at least 60%, preferably at least 80%, preferably at least 90%, preferably at least 92% of the sesquiterpenes produced.

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. *Proc Natl Acad Sci USA.*, 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, the polypeptide comprising SEQ ID NO:1 may be recombined with any other sesquiterpene synthase encoding nucleic acids, for example isolated from an organism other than *Clausena lansium*. Thus, mutant nucleic acids may be obtained and separated, which may be used for transforming a host cell according to standard procedures, for example such as disclosed in the present examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

FOX_SCH2_contig2 (SEQ ID NO: 45);
FOX_SCH2_contig3 (SEQ ID NO: 46);
FOX_SCH2_contig6 (SEQ ID NO: 47);
FOX_SCH2_contig7 (SEQ ID NO: 48);
FOX_SCH2_contig8 (SEQ ID NO: 49);
FOX_SCH2_contig9 (SEQ ID NO: 50);
FOX_SCH2_contig10 (SEQ ID NO: 51);
FOX_SCH2_contig11 (SEQ ID NO: 52);
FOX_SCH2_contig13 (SEQ ID NO: 53);
FOX_SCH2_contig14 (SEQ ID NO: 54);
FOX_SCH2_contig17 (SEQ ID NO: 55);
FOX_SCH2_contig18 (SEQ ID NO: 56);
FOX_SCH2_contig21 (SEQ ID NO: 57);
FOX_SCH2_contig23 (SEQ ID NO: 58);
FOX_SCH2_contig28 (SEQ ID NO: 59); and
FOX_SCH2_contig29 (SEQ ID NO: 60) were and aligned with the amino acid sequence of sesquiterpene synthase with the NCBI access No. AAK54279, SEQ ID NO: 61.

Figure 2:
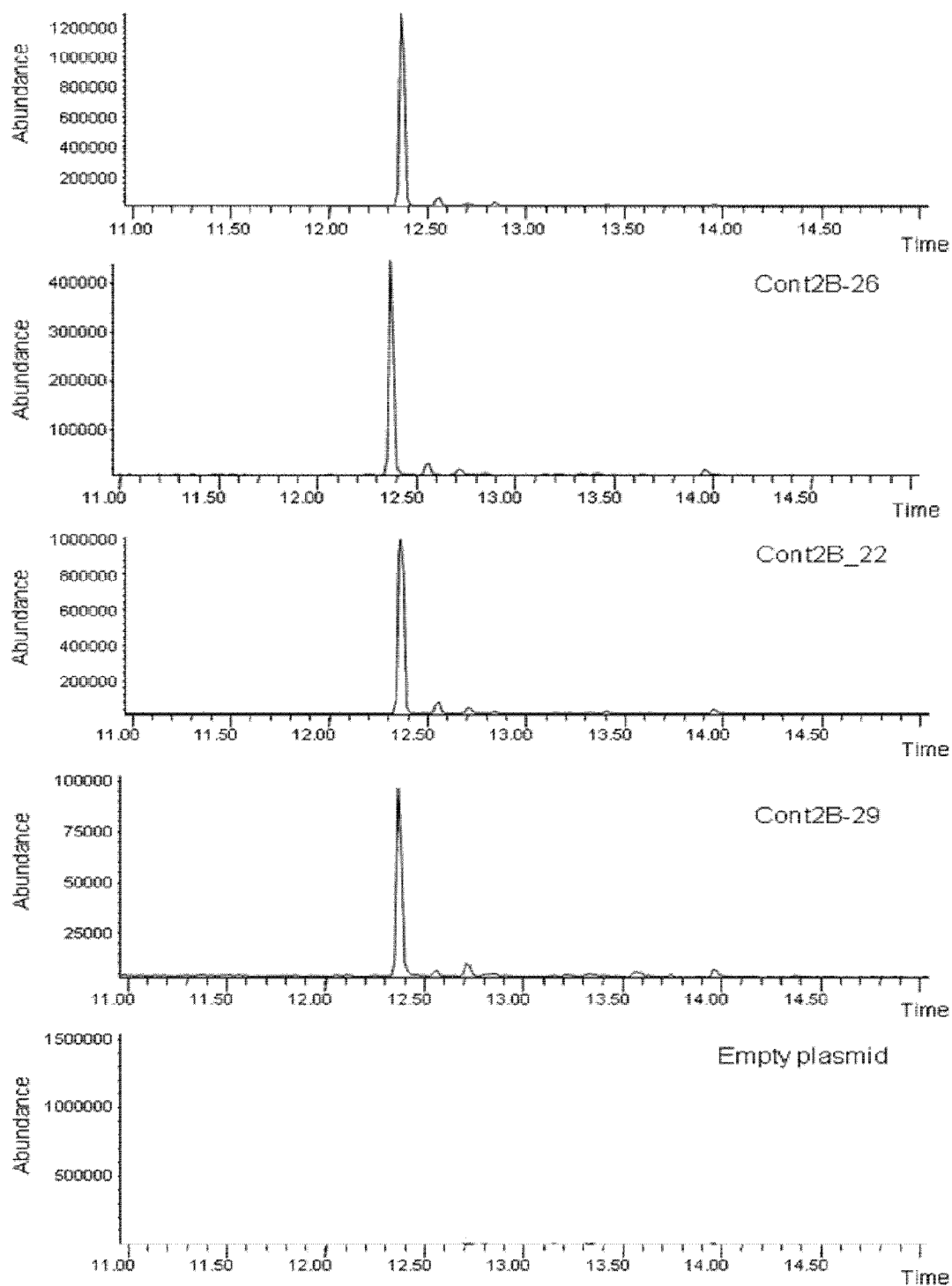

FIG. 2: Comparison of the product profiles obtained from E,E-FPP with the Cont2-1, Cont2B_22, Cont2B_26 and Cont2B_29 recombinant proteins. The analysis were made by GC-MS and the total ion chromatograms are shown.

Figure 3:
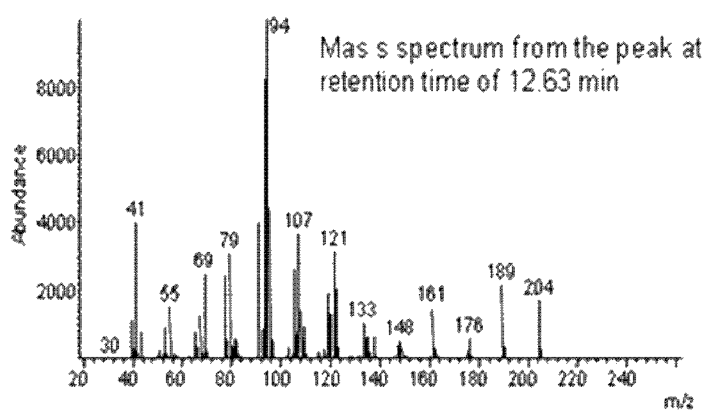
Figure 3:
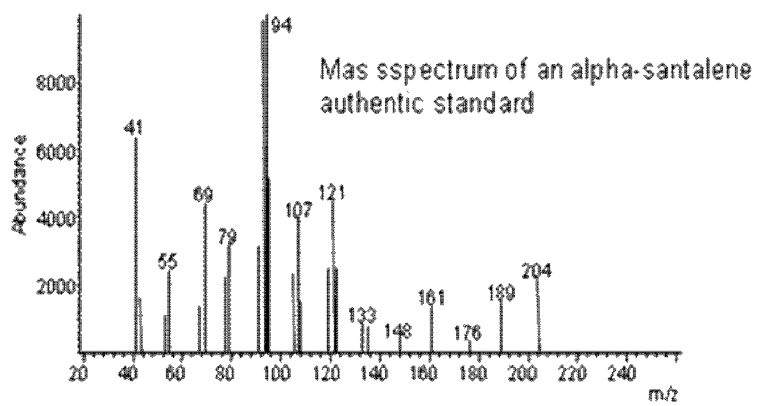

FIG. 3: Identification α-santalene by comparison of the mass spectrum from the peak at retention time of 12.63 minutes and the mass spectrum of an α-santalene authentic standard.

SPECIFIC EMBODIMENTS OF THE INVENTION OR EXAMPLES

The invention will now be described in further detail by way of the following Examples.

Example 1

Plant Material and cDNA Library Construction

Seeds of *Clausena lansium* (wampee) were obtained from farmers located in the Hainan province in China and particularly in the town of FuShan (ChengMai County) and the town of Yongxing (Haikou City). The seeds were germinated and the plants cultivated in a greenhouse.

Young leaves (1 to 2 cm long) were collected and used for the construction of a cDNA library. Total RNA was extracted from the leaves using the Concert™ Plant RNA Reagent from Invitrogen (Carlsbad, Calif.) and the mRNA were purified by oligodT-cellulose affinity chromatography using the FastTrack® 2.0 mRNA isolation Kit (Invitrogen, Carlsbad, Calif.) according to the manufacturer's instructions. A cDNA library was constructed from this mRNA and using the Marathon™ cDNA Amplification Kit (Clontech, Mountain View, Calif.).

Example 2

Massively Parallel Sequencing of the *C. lansium* Leaf cDNA Library

We used the technology of massive parallel sequencing of small DNA fragments developed by Illumina (San Diego, Calif.) to obtain sequence information of the whole cDNA library made from wampee small leaves. This sequencing technique uses a reversible terminator-based sequencing chemistry and the Cluster Station and Genome Sequencer apparatuses developed by Solexa and Illumina (www.illumina.com).

The cDNA library (1 μg) was first loaded on an agarose gel and the bands corresponding to a size between 1.5 and 3 Kb were excised, eluted and used for the sequencing. This size enrichment avoids the dilution of the library by some cDNAs encoding for proteins involved in primary metabolism (such as for example the ribulose-1,5-bisphosphate carboxylase) which often are present in high proportion in library made from plant tissues and specially green tissues. The target cDNAs, encoding for sesquiterpene synthases, typically have a size between 1.8 and 2.5 Kb and are thus included in the size enriched library.

The Ilumina technology and equipment was set up at Fasteris SA (Geneva, Switzerland) and the preparation of the DNA sample and the sequencing were performed by Fasteris S A. The cDNA library was treated using the Genomic Sample Prep Kit (Illumina). Briefly, the DNA is fragmented by nebulization, the ends are repaired to generate blunt ends, adapters are ligated to the ends of the DNA fragments and the adapter-modified DNA fragments are amplified by PCR. After controlling the quality of the library by gel electrophoresis, the generation of the DNA clusters on the flow cell and the sequencing reaction is performed on the Cluster Station and Genome Sequencer equipments. Using this technology, 1.9 millions of short sequences (reads) of at least 35 bases were obtained.

The Edena software (Dr David Hernandez, Genomic Research Laboratory, University of Geneva Hospitals, Geneva, Switzerland, unpublished result) was used to reassemble contiguous sequences. The five last bases were first removed from each read because of possible miss-incorporations due to the lower fidelity in the last cycles of the sequencing procedure. Several sets of contigs (contiguous sequences) were generated. For each set, the contigs of minimum length of 50 bases were retained. First the software parameters were set to allow assembly with 25 bases minimum overlap and either strict (100%) or non-strict (2 bases miss-match) identity. Two sets of 3634 and 3756 contigs respectively were thus generated. Another set of 4540 contigs was generated by allowing assemble with a minimum of 18 bases and non-strict overlap. The sequences of the contigs were used to search for homology with terpene synthases in publicly available protein databases using the Blastx algorithm (Altschul et al, J. Mol. Biol. 215, 403-410, 1990; http://www.ncbi.nlm.nih.gov/blast/Blast.cgi). From the three set of contigs, 14, 15 and 14 contigs were selected. Throughout the analysis of the sequences obtained from the *Clausena lansium* cDNA library, strong sequence homology was observed with sequences from citrus species, an observation consistent with the phylogenic relationship of *Clausena lansium* and Citrus species (both belonging to the Rutaceae family). Thus, the Eland software (Illumina) was used to search the non-assembled reads for DNA sequence identity with sequiterpene synthases from citrus (NCBI Accession No. CQ813507, CQ813505, CQ813508, CQ813506). From this analysis, 117 reads were selected.

Figure 1:
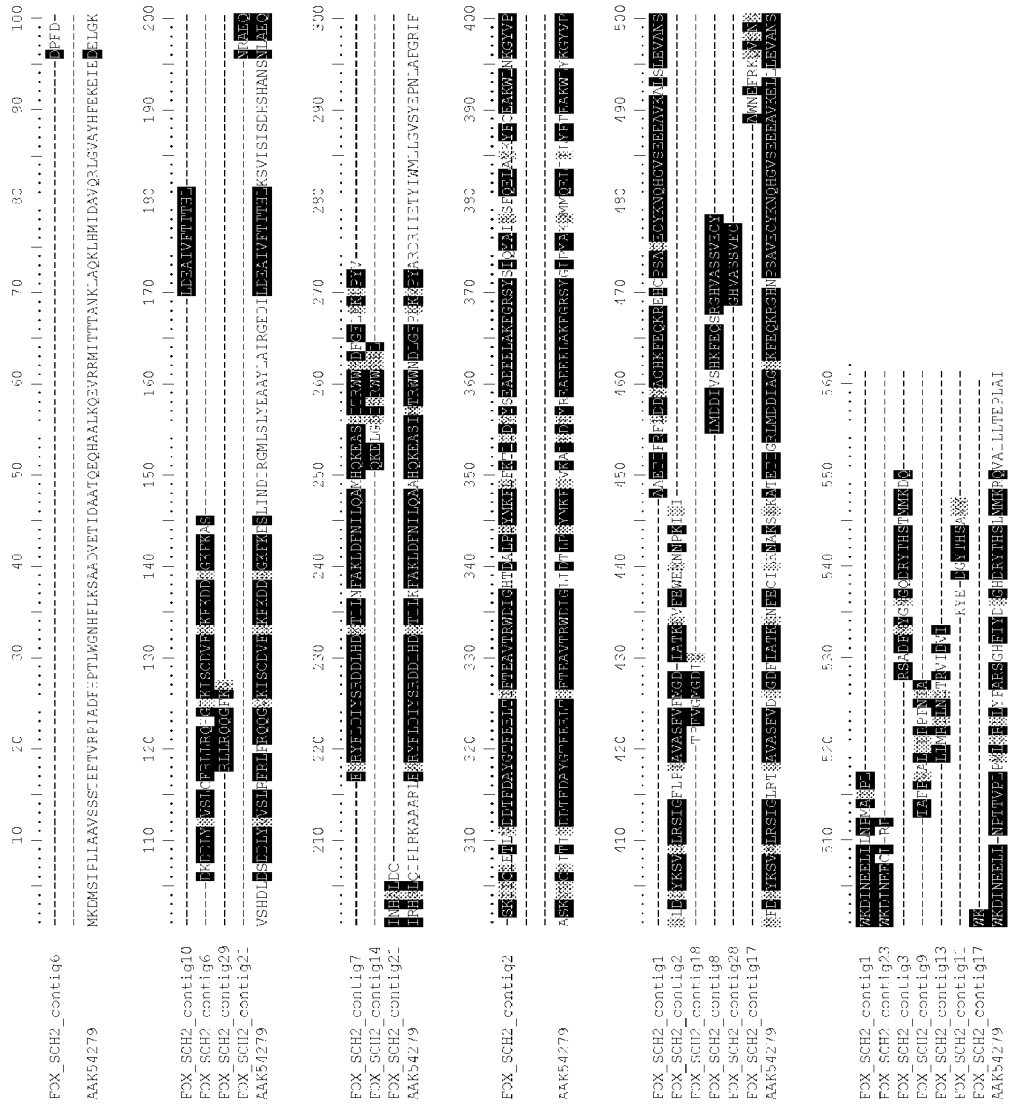
FIG. 1: Amino acid sequences deduced from the fragments of sesquiterpene synthases obtained from the sequencing of the *C. lansium* library, i.e., FOX_SCH2_contig1 (SEQ ID NO: 44)

The selected contigs and reads were then processes using the CAP program (Huang, Genomics 14(1), 18-25, 1992) and new contigs were generated. After confirmation of sequence homology with sesquiterpene synthases, 17 contigs of length from 30 to 436 bases were retained (see SEQ ID NOS:3 to 19). The deduced amino acid sequences (SEQ ID NOS:44 to 60) were aligned with a citrus sesquiterpene synthase (the *C. junos* beta-farnesene synthase, NCBI access No. AAK54279, SEQ ID NO:61) sequence in order to map their relative position along a full-length sesquiterpene synthase sequence and evaluate the number of different sesquiterpene cDNA present (FIG. 1). A set of specific oligonucleotides were designed from 6 of the 19 contigs presumably arising from distinct sesquiterpene synthases cDNAs.

Example 3

Amplification of Full-Length Sesquiterpene Synthases cDNAs

The sesquiterpene synthases-specific primers deduced from the massively parallel sequencing (Example 2) were used in combination with cDNA adaptor primers in 3'/5'RACE type PCR amplifications. The amplifications were performed using the *C. lansium* cDNA library, prepared as described above in Example 1, and the Advantage® 2 Polymerase Mix (Clontech) following the Marathon™ cDNA Amplification Kit protocol (Clontech, Mountain View, Calif.). The thermal Cycling conditions were as follows: 1 min at 94° C., 32 cycles of 1 min at 94° C. and 3 min at 68° C., and 3 min at 68° C.

Using the FS2_cont2_F1 primer (SEQ ID NO:20), a 1049 bp DNA sequence was obtained. Analysis of the sequences of several clones obtained from this amplification showed that two sequence variants were present (Cont2_RACE_F1 (SEQ ID NO:23) and Cont2_RACE_F2 (SEQ ID NO:25)) with 96% sequence identity. Each of the two sequences corresponded to the 3' end of a sesquiterpene synthase cDNA and contained a 735 bp coding region. The two deduced amino acid sequences (SEQ ID NO:24 and 26) had 92% sequence identity to each other. With the primer FS2_cont2_R1 (SEQ ID NO:21), a 1101 bp fragment (Cont2_RACE_R, SEQ ID NO:27)) was amplified containing the start codon and encoding for the 349 N-terminal amino acids of the sesquiterpene corresponding to the contig2. Alignment of the two sequences from the 3'RACE (Cont2_RACE_F1 and Cont2_RACE_F2, SEQ ID NO:23 and 25) with the sequence from the 5'RACE (cont2_RACE_R, SEQ ID NO:27) showed an overlap of 132 bases. In this overlapping region, the Cont2_RACE_F2 and Cont2_RACE_R sequences (SEQ ID NO:25 and 27) were nearly identical (one single base difference) whereas 9 bases differences were observed between the Cont2_RACE_F1 and Cont2_RACE_R sequences (SEQ ID NO:23 and 27). Thus the sequences Cont2_RACE_F2 (SEQ ID NO:25) and Cont2_RACE_R (SEQ ID NO:27) were used to reconstitute a full-length cDNA sequence (Cont2_RACE_1, SEQ ID NO:28) encoding for a 551 amino acids protein (SEQ ID NO:29).

With the FS2_Cont10_F primer (SEQ ID NO:22) two 1342 bp sequences (Cont10_RACE_Fa and Cont10_RACE_Fb, SEQ ID NO: 30 and 31) were obtained showing significant differences (67 bp, representing 95% DNA sequence identity) and suggesting the presence of two closely related sesquiterpene synthase cDNAs. The two sequences contained a 1135 bp coding region. Interestingly the sequence of Cont10_RACE_Fa (SEQ ID NO:30) was 99.9% identical to the sequence of Cont2_RACE_F2 (SEQ ID NO:25, only 1 bases difference on the 1 Kb alignment) and the sequence of Cont10_RACE_Fb (SEQ ID NO:31) was 99% identical to the sequence of Cont2_RACE_F1 (SEQ ID NO:23, only 8 bases difference on the 1 Kb alignment), thus suggesting that the DNA fragments amplified with the Cont2 and Cont10 primers allowed amplifications from two related sequences with no real discrimination. Two primers (Cont2_start (SEQ ID NO:32) and Cont2_stop (SEQ ID NO:33)), which are specific to the regions of the start and the stop codons of the sequences from the 5'RACE and the 3'RACE of the cont2 and cont10 fragments, were designed in order to amplify simultaneously the two or more corresponding full-length cDNAs. The primer Cont2_start (SEQ ID NO:32) was extended with the CACC sequence to allow direct insertion into the pET101/D-TOPO plasmid (Invitrogen). The amplification was first performed using the Advantage® 2 Polymerase Mix (Clontech). Each PCR mixture contained, in a total volume of 50 µL, 5 µL of Advantage® 2 PCR Buffer, 200 µM dNTPs, 200 nM each oligonucleotide primer, 5 µL of 100 fold diluted cDNA and 1 µL of Advantage® 2 Polymerase Mix. The thermal cycling conditions were as follows: 2 min at 95° C.; 35 cycles of 30 sec at 95° C., 30 sec at 60° C. and 4 min at 72° C.; and 10 min at 72° C. A second round of amplification was then performed using 5 µl of the purified PCR product from the first round of amplification and using the Pfu DNA polymerase (Promega), in a final volume of 50 µl containing 5 µl of Pfu DNA polymerase 10× buffer, 200 µM each dNTP, 0.4 µM each forward and reverse primer, 2.9 units Pfu DNA polymerase. The thermal cycling conditions were identical to the conditions used in the first round. The purified PCR products were ligated in the pET1001/D-TOPO vector following the manufacturer's instructions (Invitrogen). Several clones were selected and after sequencing of the insert, some variations in the sequences were observed. The following clones were selected: Cont2-1 (SEQ ID NO:2), Cont2B_22 (SEQ ID NO:38), Cont2B_26 (SEQ ID NO:39) and Cont2B_29 (SEQ ID NO:40). The sequences of the proteins encoded by these clones are provided in SEQ ID NO:1 and 41 to 43, respectively.

Example 4

Heterologous Expression and Enzymatic Activities of the Recombinant Sesquiterpene Synthases The plasmids pET101 with Cont2_1 (SEQ ID NO:2), Cont2B_22 (SEQ ID NO:38), Cont2B_26 (SEQ ID NO:39) and Cont2B_29 (SEQ ID NO:40) prepared as described in Example 3 were transformed into Bl21(DE3) *E. Coli* cells. Single colonies of transformed cells were used to inoculate 5 ml LB medium. After 5 to 6 hours incubation at 37° C., the culture was transferred to a 20° C. incubator and left 1 hour for equilibration. Expression of the protein was then induced by the addition of 1 mM IPTG and the culture was incubated over-night at 20° C. The next day, the cells were collected by centrifugation, re-suspended in 0.1 volume of 50 mM MOPSO pH 7, 10% glycerol, 1 mM DTT and lysed by sonication. The extract was cleared by centrifugation (30 min at 20,000 g), and the supernatant containing the soluble protein was used for further experiments.

The crude protein extract was used to evaluate the enzymatic activity. The enzymatic assay was performed in a Teflon sealed glass tube using 50 to 100 µl of protein extract in a final volume of 1 mL of 50 mM MOPSO pH 7, 10% glycerol supplemented with 1 mM DTT, 20 mM $MgCl_2$ and 50 to 200 µM purified E,E-farnesyl diphosphate (FPP) (prepared as described by Keller and Thompson, J. Chromatogr 645(1), 161-167, 1993). The tube was incubated 18 to 24 hours at 30° C. and the enzyme products were extracted twice with one volume of pentane. After concentration under a nitrogen flux, the extract was analyzed by GC and the identity of the products was confirmed by GC-MS based on the concordance of the retention indices and mass spectra of authentic standards. The GC-MS analysis was performed on a Hewlett-Packard 6890 Series GC system equipped with a flame ionization detector using a 0.25 mm inner diameter by 30 m SPB-1 capillary column (Supelco, Bellefonte, Pa.). The carrier gas was He at a constant flow of 1.5 mL/min. The initial oven temperature was 80° C. followed by a gradient of 10° C./min to 280° C. The spectra were recorded at 70 eV with an electron multiplier voltage of 2200V.

The assay revealed the formation of (+)-α-santalene as a major product (92.7% of the total sesquiterpenes produced) and traces amounts of five additional sesquiterpenes accounting for 4.8 to 0.95% of the enzyme products. (+)-α-santalene was identified with GC-MS analysis by coincidence of the mass spectrum and of the retention index with published values (Joulain, D., and König, W. A. The Atlas of Spectral Data of Sesquiterpene Hydrocarbons, E B Verlag, Hamburg, 1998). The identification of (+)-α-santalene was further confirmed by $^1$H NMR, $^{13}$C NMR and by measurement of the optical rotation. To produce sufficient quantities for these measurements, the enzymatic assay described above was scaled up to 1 L. The enzyme products were extracted with an equal volume of pentane, concentrated and the sesquiterpene hydrocarbons fraction (5.5 mg) purified by filtration on a short silica column. spectral data obtained with Cont2_1 is provided in FIG. 2.

The NMR spectrum was recorded on a Bruker-Avance-500 spectrometer. The NMR data is the following:

$^1$H NMR (500.13 MHz, CDCl$_3$): δ0.82 (s, 2H), 0.83 (s, 3H), 0.99 (s, 3H), 1.00-1.08 (m, 2H), 1.08-1.26 (m, 2H), 1.57-1.63 (m, 6H), 1.68 (s, 3H), 5.12 (txq, J=7.2, 1.4 Hz, 1H)

$^{13}$C NMR (125.76 MHz, CDCl$_3$): δ10.7 (q), 17.5 (q), 19.6 (d), 23.3 (t), 25.7 (q), 27.4 (s), 31.0 (t), 31.5 (t), 34.6 (t), 38.2 (d), 45.9 (s), 125.5 (d), 130.8 (s);

The fact that the (+)-α-santalene stereoisomer was produced has been evidenced by measuring the optical rotation (as measured on a Perkin-elmer 241 polarimeter): $[\alpha]_D^{20}$=+ 12.0 (C=0.3, CHCl$_3$).

Example 5

In-Vivo Production of (+)-α-Santalene in *E coli*

The use of the *C. lansium* santalene synthase for the in-vivo production of sesquiterpenes in *E coli* cells was evaluated by co-expressing the sesquiterpene synthase with a FPP synthase and the enzymes of a four step biosynthetic pathway allowing the conversion of mevalonate to FPP. The mevalonate pathway genes were organized in a single operon and encoded for a mevalonate kinase (mvaK1), a phosphomevalonate kinase (mvaK2), a mevalonate diphosphate decarboxylase (MvaD) and an isopentenyl diphosphate isomerase (idi), all the enzymes converting exogenous mevalonate to isopentenyl diphosphate (IPP) and dimethylallyl diphosphate (DMAPP), the two substrates of the FPP synthase. The co-expression of this partial mevalonate pathway was used to increase the amount of intracellular FPP available for the sesquiterpene synthase and thus the quantities of sesquiterpene produced.

The yeast FPP synthase gene (Accession number J05091) was amplified from *S. cerevisiae* genomic DNA using the primers FPPy_NcoI (SEQ ID NO:34) and FPPy-Eco (SEQ ID NO:35). The genomic DNA was isolated from *S. cerevisiae* using the Qiagen RNA/DNA Maxi Kit (Qiagen AG, Basel, Switzerland). The PCR was performed with the Pfu DNA polymerase (Promega AG, Dubendorf, Switzerland) in a final volume of 50 µl containing 0.4 µl of each primer, 200 µM dNTPs, 0.5 µl DNA polymerase 5 µl *S. cerevisiae* genomic DNA. The PCR cycling condition were as follows: 90 sec at 95° C.; 28 cycles of 45 sec at 95° C., 30 sec at 54° C. and 4 min at 72° C.; 10 min at 72° C. The amplified DNA was ligated as NdeI-EcoRI fragment in the first multi cloning site (MCS1) of the pACYCDuet-1 plasmid (Novagen, Madison, Wis.) providing the plasmid pACYCDuet-FPPs harbouring the FPPs gene under the control of a T7 promoter.

An operon containing the genes encoding for mvaK1, mvaK2, MvaD and idi was amplified from genomic DNA of *Streptococcus pneumoniae* (ATCC BAA-334, LGC Standards, Molsheim, France) with the primers MVA-up1-start (SEQ ID NO:36) and MVA-up2-stop (SEQ ID NO:37). The PCR was performed using the PfuUltra™ II Fusion HS DNA polymerase (Stratagene, Agilent Technologies Inc., Santa Clara, Calif., USA). The composition of the PCR mix was according to the manufacturer's instructions. The thermal cycling conditions were 2 min at 95° C.; 30 cycles of 20 sec at 95° C., 20 sec at 58° C. and 90 sec at 72° C.; and 3 min at 72° C. The 3.8 Kb fragment was purified on an agarose gel and ligated using the In-Fusion™ Dry-Down PCR Cloning Kit (Clontech Laboratories) into the second MCS of the pACYCDuet-FPPs plasmid digested with NdeI and XhoI providing the plasmid pACYCDuet-4506. The sequences of the two inserts were fully sequenced to exclude any mutation.

BL21 Star™ (DE3) *E. coli* cells (Invitrogen, Carlsbad, Calif.) were transformed with the plasmids pET101-cont2_1 (SEQ ID NO:2) prepared as described in Example 3 and with the plasmid pACYCDuet-4506. Transformed cells were selected on carbenicillin (50 µg/ml) and chloramphenicol (34 µg/ml) LB-agarose plates. Single colonies were used to inoculate 5 mL liquid LB medium supplemented with the same antibiotics. The culture was incubated overnight at 37° C. The next day 2 mL of TB medium supplemented with the same antibiotics were inoculated with 0.2 mL of the overnight culture. After 6 hours incubation at 37° C., the culture was cooled down to 28° C. and 1 mM IPTG, 2 mg/mL mevalonate (prepared by dissolving mevalonolactone (Sigma) in 0.5N NaOH at a concentration of 1 g/mL and incubating the solution for 30 min at 37° C.) and 0.2 ml decane were added to each tube. The cultures were incubated for 48 hours at 28° C. The cultures were then extracted twice with 2 volumes of ethyl-acetate, the organic phase was concentrated to 500 µL and analyzed by GC-MS as described above in Example 4. In these conditions the cells produced (+)-α-santalene at 250 mg/L culture in 48 hours.

This example shows that an *E. coli* cell transformed with an α-santalene synthase, as defined in the present invention, is capable of producing α-santalene. The other enzymes with which the *E. coli* cell is transformed are not essential for the production of α-santalene. Indeed α-santalene is also produced when an *E. coli* cell is transformed with the α-santalene synthase only, but in lower amounts. The other enzymes with which the *E. coli* cell is transformed are added for the only purpose of increasing the amount of precursor available to the α-santalene synthase.

SEQUENCE LISTING

<160> NUMBER OF SEQ ID NOS: 61

<210> SEQ ID NO 1
<211> LENGTH: 551
<212> TYPE: PRT
<213> ORGANISM: Clausena lansium

<400> SEQUENCE: 1

```
Met Ser Thr Gln Gln Val Ser Glu Asn Ile Val Arg Asn Ala Ala
1               5                   10                  15

Asn Phe His Pro Asn Ile Trp Gly Asn His Phe Leu Thr Cys Pro Ser
                20                  25                  30

Gln Thr Ile Asp Ser Trp Thr Gln Gln His His Lys Glu Leu Lys Glu
            35                  40                  45

Glu Val Arg Lys Met Met Val Ser Asp Ala Asn Lys Pro Ala Gln Arg
        50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110

Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
    130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
                165                 170                 175

Val Ser Asn Ser Pro Val Asn Ser Thr Phe Ala Glu Gln Ile Arg His
            180                 185                 190

Ser Leu Arg Val Pro Leu Arg Lys Ala Val Pro Arg Leu Glu Ser Arg
        195                 200                 205

Tyr Phe Leu Asp Ile Tyr Ser Arg Asp Asp Leu His Asp Lys Thr Leu
    210                 215                 220

Leu Asn Phe Ala Lys Leu Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
            260                 265                 270

Ile Leu Val Gly Val Ser Tyr Gln Pro Lys Phe Ser Thr Gly Arg Ile
        275                 280                 285

Phe Leu Ser Lys Ile Ile Cys Leu Glu Thr Leu Val Asp Asp Thr Phe
    290                 295                 300

Asp Ala Tyr Gly Thr Phe Asp Glu Leu Ala Ile Phe Thr Glu Ala Val
305                 310                 315                 320

Thr Arg Trp Asp Leu Gly His Arg Asp Ala Leu Pro Glu Tyr Met Lys
                325                 330                 335

Phe Ile Phe Lys Thr Leu Ile Asp Val Tyr Ser Glu Ala Glu Gln Glu
            340                 345                 350

Leu Ala Lys Glu Gly Arg Ser Tyr Ser Ile His Tyr Ala Ile Arg Ser
        355                 360                 365
```

```
Phe Gln Glu Leu Val Met Lys Tyr Phe Cys Glu Ala Lys Trp Leu Asn
370                 375                 380

Lys Gly Tyr Val Pro Ser Leu Asp Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
                420                 425                 430

Ile Ile Ile Ala Ala Glu Thr Ile Phe Arg Phe Leu Asp Asp Ile Ala
                435                 440                 445

Gly His Arg Phe Glu Gln Lys Arg Glu His Ser Pro Ser Ala Ile Glu
450                 455                 460

Cys Tyr Lys Asn Gln His Gly Val Ser Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Leu Gln Val Ile Leu
                500                 505                 510

Asp Leu Ser Arg Ser Ala Asp Phe Met Tyr Gly Asn Ala Gln Asp Arg
                515                 520                 525

Phe Thr His Ser Thr Met Met Lys Asp Gln Val Asp Leu Val Leu Lys
530                 535                 540

Asp Pro Val Lys Leu Asp Asp
545                 550
```

```
<210> SEQ ID NO 2
<211> LENGTH: 1656
<212> TYPE: DNA
<213> ORGANISM: Clausena lansium

<400> SEQUENCE: 2
```

| | | | | | |
|---|---|---|---|---|---|
| atgtcaactc | aacaagtttc | atcagagaac | attgttcgta | acgctgcgaa | tttccatcct | 60 |
| aatatatggg | gaaaccattt | cctcacatgt | ccttctcaga | cgattgatag | ttggactcaa | 120 |
| cagcaccaca | aagaactgaa | agaagaggtg | aggaaaatga | tggtgtctga | tgcaaataaa | 180 |
| cctgcccaga | gattgcgctt | gattgatact | gtccaaaggc | taggtgtggc | ttaccacttt | 240 |
| gaaaaggaga | ttgatgatgc | attggagaaa | ataggtcatg | accctttga | tgataaagat | 300 |
| gatctctaca | ttgtctctct | ttgttttcga | ttgctgaggc | agcatggaat | taagatatca | 360 |
| tgtgatgtgt | ttgagaagtt | taaagatgac | gatggaaaat | tcaaggcatc | attgatgaat | 420 |
| gatgttcaag | gcatgctaag | tttatatgag | gcagcacacc | tagccattca | cggagaagat | 480 |
| attttagatg | aagcaattgt | tttcacgacc | actcaccta | agtcaacggt | atctaattct | 540 |
| cctgtaaact | ctactttgc | tgaacaaata | cgtcattctc | tcagagttcc | tctccgtaaa | 600 |
| gctgtaccta | ggttagagtc | gaggtatttc | ttggatatct | attcaagaga | tgatttgcac | 660 |
| gataaaactt | tgctcaattt | cgcaaagtta | gactttaata | tactacaagc | aatgcaccag | 720 |
| aaggaagcaa | gtgagatgac | caggtggtgg | agagattttg | acttccttaa | aaagctgcct | 780 |
| tatataagag | acagagtcgt | ggagctatat | ttttggattc | tggtgggagt | gtcttatcag | 840 |
| cccaaattca | gcactggtag | aatttttttg | tccaaaataa | tatgccttga | gaccctcgta | 900 |
| gatgatacat | ttgacgccta | cggtactttt | gacgagctcg | caatctttac | tgaagcagtt | 960 |
| acaagatggg | accttggcca | cagagatgca | ctaccagaat | acatgaaatt | catttttcaag | 1020 |
| acactcattg | atgtctacag | tgaagctgag | caagaactgg | caaggaagg | gagatcatac | 1080 |

-continued

```
agcatacact atgcaatacg atcgttccaa gaactagtta tgaagtactt ctgcgaagcc   1140
aagtggttaa ataaaggtta tgttccgagc ctggacgatt ataaatcagt ttcattaaga   1200
agtatcggtt ttttaccgat agcggtagct tccttcgttt tcatgggtga tattgcaact   1260
aaggaggtct ttgaatggga aatgaataac cctaagatca taatagccgc agaaacgatt   1320
ttcagattcc tggatgacat agcaggccat aggtttgagc aaaagagaga acatagtcca   1380
tcagctattg aatgctacaa gaatcaacat ggagtgtctg aggaagaggc agttaaagcg   1440
ttgtcgttag aagttgctaa tagttggaaa gatataaatg aggagctgct tctcaaccca   1500
atggctattc ctttacctct gcttcaggtg attcttgatc tctcacgttc ggccgatttt   1560
atgtacggta atgctcaaga tcgcttcacg cattcaacga tgatgaaaga ccaagttgat   1620
ttggtgctga aggaccccgt taagcttgac gattaa                             1656
```

```
<210> SEQ ID NO 3
<211> LENGTH: 211
<212> TYPE: DNA
<213> ORGANISM: Clausena lansium

<400> SEQUENCE: 3
gccgcagaaa cgattttcag attcctggat gatgtagcag gccataagtt tgagcaaaag     60
agagaacatt gtccatcagc tattgaatgc tacaagaatc aacatggagt gtctgaggaa    120
gaggcagtta aagcgttgtc gttagaagtt gctaatagtt ggaaagatat aaatgaggag    180
ctgcttctca acccaatggc tattccttta c                                   211
```

```
<210> SEQ ID NO 4
<211> LENGTH: 436
<212> TYPE: DNA
<213> ORGANISM: Clausena lansium

<400> SEQUENCE: 4
gtccaaaata atatgccttg agaccctcgt agatgataca tttgacgcct acggtacttt     60
tgaagagctc acaatcttta ctgaagcagt tacaagatgg gacattggcc acacagatgc    120
actaccagat tacatgaaat tccttttcaa gacactcatt gatgtctata gtgaagctga    180
ggaagaactg gcaaaggaag gaagatcata cagcatacaa tatgcaatac gatcgtttca    240
agaactagct atgaaatact tctgcgaagc caagtggtta aataaaggtt atgttccgag    300
cctggacgat tataaatcag tttcattaag aagtatcggt tttttaccga tagcggtagc    360
ttccttcgtt ttcatgggtg atattgcaac taaggaggtc tttgaatggg aaatgaataa    420
ccctaagatc ataata                                                    436
```

```
<210> SEQ ID NO 5
<211> LENGTH: 71
<212> TYPE: DNA
<213> ORGANISM: Clausena lansium

<400> SEQUENCE: 5
cacgttcggc cgattttatg tacggcaatg gtcaagatcg ctacacgcat tcaacgatga     60
tgaaagacca a                                                          71
```

```
<210> SEQ ID NO 6
<211> LENGTH: 133
<212> TYPE: DNA
<213> ORGANISM: Clausena lansium
```

<400> SEQUENCE: 6
tgaccctttt gatgataaag atgatctcta cattgtctct ctttgttttc gattgctgag      60
gcagcatgga attaagatat catgtgatgt gtttgagaag tttaaagatg acgatggaaa     120
attcaaggca tcc                                                        133

<210> SEQ ID NO 7
<211> LENGTH: 172
<212> TYPE: DNA
<213> ORGANISM: Clausena lansium

<400> SEQUENCE: 7
agagtcgagg tatttcttgg atatctattc aagagatgat ttgcacgata aaactttgct      60
caatttcgca aagttagact ttaatatact acaagcaatg caccagaagg aagcaagtga     120
gataaccagg tggtggagag attttggatt ccttgaaaag ctgccttatg ta             172

<210> SEQ ID NO 8
<211> LENGTH: 73
<212> TYPE: DNA
<213> ORGANISM: Clausena lansium

<400> SEQUENCE: 8
actaatggat gacatagtgt cacacaagtt tgaacaaagc agagggcacg ttgcctcgag      60
cgttgagtgt tac                                                        73

<210> SEQ ID NO 9
<211> LENGTH: 46
<212> TYPE: DNA
<213> ORGANISM: Clausena lansium

<400> SEQUENCE: 9
actgcttttc ctgtggcttt aattgagaga cctttcaata tcgcac                    46

<210> SEQ ID NO 10
<211> LENGTH: 47
<212> TYPE: DNA
<213> ORGANISM: Clausena lansium

<400> SEQUENCE: 10
cacttcttat gcgaattctc aatcttacgc gcgttataga tgtcatt                   47

<210> SEQ ID NO 11
<211> LENGTH: 44
<212> TYPE: DNA
<213> ORGANISM: Clausena lansium

<400> SEQUENCE: 11
ccagaaggaa ctcggtgaca tttcaaggtg gtggaaagaa ttag                      44

<210> SEQ ID NO 12
<211> LENGTH: 42
<212> TYPE: DNA
<213> ORGANISM: Clausena lansium

<400> SEQUENCE: 12
gcatggaatg agttccggaa acaagtttca aatgcctgga ag                        42

<210> SEQ ID NO 13
<211> LENGTH: 39
<212> TYPE: DNA
<213> ORGANISM: Clausena lansium

```
<400> SEQUENCE: 13
taatcgtgct gaacaaatta atcatgctct cgactgtcc                             39

<210> SEQ ID NO 14
<211> LENGTH: 38
<212> TYPE: DNA
<213> ORGANISM: Clausena lansium

<400> SEQUENCE: 14
aagtatgaag atggctacac tcattctgca gttgtgct                              38

<210> SEQ ID NO 15
<211> LENGTH: 38
<212> TYPE: DNA
<213> ORGANISM: Clausena lansium

<400> SEQUENCE: 15
ttttagatga agcaattgtt ttcacgacca ctcacctt                              38

<210> SEQ ID NO 16
<211> LENGTH: 37
<212> TYPE: DNA
<213> ORGANISM: Clausena lansium

<400> SEQUENCE: 16
cctggaagga tataaacgag gagtgcctac gcccaac                               37

<210> SEQ ID NO 17
<211> LENGTH: 30
<212> TYPE: DNA
<213> ORGANISM: Clausena lansium

<400> SEQUENCE: 17
acaccttttg ttggcatggg agacattgta                                       30

<210> SEQ ID NO 18
<211> LENGTH: 30
<212> TYPE: DNA
<213> ORGANISM: Clausena lansium

<400> SEQUENCE: 18
gagggcacgt tgcctcaagc gtagagtgtt                                       30

<210> SEQ ID NO 19
<211> LENGTH: 30
<212> TYPE: DNA
<213> ORGANISM: Clausena lansium

<400> SEQUENCE: 19
cgactgctta ggcagcaagg atttaaggtt                                       30

<210> SEQ ID NO 20
<211> LENGTH: 31
<212> TYPE: DNA
<213> ORGANISM: Artificial sequence
<220> FEATURE:
<223> OTHER INFORMATION: Primer

<400> SEQUENCE: 20
cttgagaccc tcgtagatga tacatttgac g                                     31

<210> SEQ ID NO 21
```

-continued

```
<211> LENGTH: 31
<212> TYPE: DNA
<213> ORGANISM: Artificial sequence
<220> FEATURE:
<223> OTHER INFORMATION: Primer

<400> SEQUENCE: 21
gtatgatctt ccttcctttg ccagttcttc c                              31

<210> SEQ ID NO 22
<211> LENGTH: 31
<212> TYPE: DNA
<213> ORGANISM: Artificial sequence
<220> FEATURE:
<223> OTHER INFORMATION: Primer

<400> SEQUENCE: 22
gatgaagcaa ttgttttcac gaccactcac c                              31

<210> SEQ ID NO 23
<211> LENGTH: 1049
<212> TYPE: DNA
<213> ORGANISM: Clausena lansium

<400> SEQUENCE: 23
cctatggtac tcttgaagag ctcacagtct ttactgaagc aattacaaga tgggacgttg      60
gccacacaga tgcactacca gattacatga aattcctttt caagacactc attgatgtct    120
atagtgaagc tgaggaagaa ctggcaaagg aaggaagatc atacagcata caatatgcaa    180
tacgatcgtt tcaagaacta gctatgaaat acttctgcga agcggagtgg ttaaataaag    240
gttatgttcc gagcctggac gagtataaat cagtttcagt aagaagtgtc ggttttttc    300
cgatagcggt agcttccttc gttttcatgg gtgatattgc aactaaggag gtctttgaat    360
gggaaatgaa taaccctaag atcataatag ccgcagaaac gattttcaga ttcctggatg    420
atgcagcagg ccataagttt gagcaaaaga gagaacattg tccatcagct attgaatgct    480
acaagaatca acatggagtg tctgaggaag aggcagttaa agcgttgtcg ttagaagttg    540
ctaatagttg gaaagatata aatgaggagc tgcttctcaa cccaatggct attcctttac    600
ctctacttca ggtgattctt gatctctcac gttcggccga ttttatgtac ggcaatggtc    660
aagatcgcta cacgcattca acgatgatga agaccaagt tgacttggtg ctgaaggacc    720
ccgttaagct tgacgattaa agttatgttg ctgatttcct atcgtatatt tgagaagttg    780
gtaataaatt aagttggtgc ttgctagtta tttagctagc tagtcatgcg tagctaaggg    840
atggttcaat tgattaggcc tatattctag taaaaataaa aggagtaaga acgaatctcc    900
ctcacaccaa cttcgcaata atgtaatta tttcatctat gtctgttaca aaaattttga    960
gattaaaata aacagcaatc ctacttgcat ggaataaaca ataataccat ttttactaat   1020
aaaaaaaaaa aaaaaaaaa aaaaaaaa                                       1049

<210> SEQ ID NO 24
<211> LENGTH: 245
<212> TYPE: PRT
<213> ORGANISM: Clausena lansium

<400> SEQUENCE: 24

Tyr Gly Thr Leu Glu Glu Leu Thr Val Phe Thr Glu Ala Ile Thr Arg
1               5                   10                  15

Trp Asp Val Gly His Thr Asp Ala Leu Pro Asp Tyr Met Lys Phe Leu
            20                  25                  30
```

Phe Lys Thr Leu Ile Asp Val Tyr Ser Glu Ala Glu Glu Leu Ala
         35                  40                  45

Lys Glu Gly Arg Ser Tyr Ser Ile Gln Tyr Ala Ile Arg Ser Phe Gln
 50                  55                  60

Glu Leu Ala Met Lys Tyr Phe Cys Glu Ala Trp Leu Asn Lys Gly
 65                  70                  75                  80

Tyr Val Pro Ser Leu Asp Glu Tyr Lys Ser Val Ser Val Arg Ser Val
                 85                  90                  95

Gly Phe Phe Pro Ile Ala Val Ala Ser Phe Val Phe Met Gly Asp Ile
                100                 105                 110

Ala Thr Lys Glu Val Phe Glu Trp Glu Met Asn Asn Pro Lys Ile Ile
             115                 120                 125

Ile Ala Ala Glu Thr Ile Phe Arg Phe Leu Asp Ala Ala Gly His
             130                 135                 140

Lys Phe Glu Gln Lys Arg Glu His Cys Pro Ser Ala Ile Glu Cys Tyr
145                 150                 155                 160

Lys Asn Gln His Gly Val Ser Glu Glu Ala Val Lys Ala Leu Ser
                 165                 170                 175

Leu Glu Val Ala Asn Ser Trp Lys Asp Ile Asn Glu Glu Leu Leu Leu
             180                 185                 190

Asn Pro Met Ala Ile Pro Leu Pro Leu Leu Gln Val Ile Leu Asp Leu
             195                 200                 205

Ser Arg Ser Ala Asp Phe Met Tyr Gly Asn Gly Gln Asp Arg Tyr Thr
         210                 215                 220

His Ser Thr Met Met Lys Asp Gln Val Asp Leu Val Leu Lys Asp Pro
225                 230                 235                 240

Val Lys Leu Asp Asp
             245

<210> SEQ ID NO 25
<211> LENGTH: 906
<212> TYPE: DNA
<213> ORGANISM: Clausena lansium

<400> SEQUENCE: 25
cctacggtac ttttgacgag ctcacaatct ttactgaagc agttacaaga tgggacattg      60
gccacagaga tgcactacca gaatacatga aattcatttt caagacactc attgatgtct     120
acagtgaagc tgagcaagaa ctggcaaagg aagggagatc atacagcata caatatgcaa     180
tacgatcgtt ccaagaacta gttatgaagt acttctgcga agccaagtgg ttaaataaag     240
gttatgttcc gagcctggac gattataaat cagtttcatt aagaagtatc ggttttttac     300
cgatagcggt agcttccttc gttttcatgg gtgatattgc aactaaggag gtctttgaat     360
gggaaatgaa taaccctaag atcataatag ccgcagaaac gattttcaga ttcctggatg     420
acatagcagg ccataagttt gagcaaaaga gaacatag tccatcagct attgaatgct      480
acaagaatca acatggagtg tctgaggaag aggcagttaa agcgttgtcg ttagaagttg     540
ctaatagttg gaaagatata aatgaggagc tgcttctcaa cccaatggct attcctttac     600
ctctgcttca ggtgattctt gatctctcac gttcggccga ttttatgtac ggtaatgctc     660
aagatcgctt cacgcattca acgatgatga agaccaagt tgatttggtg ctgaaggacc     720
ccgttaagct tgacgattaa agttatgttg ctgatttcct atcgtatatt tgagaagttg     780
gtaataaatt aagttggtgc ttgctagtta tttagctagc tagtcatgcg tagctagggg     840

```
atggttcaat tgattaggcc tatattctag taaaaataaa cgatgtaaga acaaatctcc      900
ctcgca                                                                906
```

<210> SEQ ID NO 26
<211> LENGTH: 245
<212> TYPE: PRT
<213> ORGANISM: Clausena lansium

<400> SEQUENCE: 26

```
Tyr Gly Thr Phe Asp Glu Leu Thr Ile Phe Thr Glu Ala Val Thr Arg
1               5                   10                  15

Trp Asp Ile Gly His Arg Asp Ala Leu Pro Glu Tyr Met Lys Phe Ile
            20                  25                  30

Phe Lys Thr Leu Ile Asp Val Tyr Ser Glu Ala Glu Gln Glu Leu Ala
        35                  40                  45

Lys Glu Gly Arg Ser Tyr Ser Ile Gln Tyr Ala Ile Arg Ser Phe Gln
    50                  55                  60

Glu Leu Val Met Lys Tyr Phe Cys Glu Ala Lys Trp Leu Asn Lys Gly
65                  70                  75                  80

Tyr Val Pro Ser Leu Asp Asp Tyr Lys Ser Val Ser Leu Arg Ser Ile
                85                  90                  95

Gly Phe Leu Pro Ile Ala Val Ala Ser Phe Val Phe Met Gly Asp Ile
            100                 105                 110

Ala Thr Lys Glu Val Phe Glu Trp Glu Met Asn Asn Pro Lys Ile Ile
        115                 120                 125

Ile Ala Ala Glu Thr Ile Phe Arg Phe Leu Asp Asp Ile Ala Gly His
    130                 135                 140

Lys Phe Glu Gln Lys Arg Glu His Ser Pro Ser Ala Ile Glu Cys Tyr
145                 150                 155                 160

Lys Asn Gln His Gly Val Ser Glu Glu Glu Ala Val Lys Ala Leu Ser
                165                 170                 175

Leu Glu Val Ala Asn Ser Trp Lys Asp Ile Asn Glu Glu Leu Leu Leu
            180                 185                 190

Asn Pro Met Ala Ile Pro Leu Pro Leu Leu Gln Val Ile Leu Asp Leu
        195                 200                 205

Ser Arg Ser Ala Asp Phe Met Tyr Gly Asn Ala Gln Asp Arg Phe Thr
    210                 215                 220

His Ser Thr Met Met Lys Asp Gln Val Asp Leu Val Leu Lys Asp Pro
225                 230                 235                 240

Val Lys Leu Asp Asp
                245
```

<210> SEQ ID NO 27
<211> LENGTH: 1101
<212> TYPE: DNA
<213> ORGANISM: Clausena lansium

<400> SEQUENCE: 27

```
ctagtagcta aaaaaattat taagttcaat cttttttgtc tgtctagaga agatgtcaa       60 ctcaacaagt tcatcagag aacattgttc gtaatgctgc agatttccat cctaatatat      120
ggggaaacca tttcctcaca tgtctttctc aaacgattga tagttggact caacagcacc    180
acaaagaact gaagaagag gtgaggaaaa tgatggtgtc tgatgcaaat aaacctgccc     240
agagattgcg cttgattgat actgtccaaa ggttaggtgt ggcttaccac tttgaaaagg    300
agattgatga tgcattggag aaaataggtc atgacccttt tgatgataaa gatgatctct    360
```

```
acattgtctc tctttgtttt cgattgctga ggcagcatgg aattaagata tcatgtgatg      420
tgtttgagaa gtttaaagat gacgatggaa aattcaaggc atcattgatg aatgatgttc      480
aaggcatgct aagtttatat gaggcagcac acctagccat tcacggagaa gatattttag     540
atgaagcaat tgttttcacg accactcacc ttaagtcaac ggtatctaat tctcctgtaa      600
actctacttt tgctgaacaa atacgtcatt ctctcagagt tcctctccgt aaagctgtac     660
ctaggttaga gtcgaggtat ttcttggata tctattcaag agatgatttg cacgataaaa     720
ctttgctcaa tttcgcaaag tcagacttta atatactaca agcaatgcac cagaaggaag     780
caagtgagat gaccaggtgg tggagagatt ttgacttcct taaaaagctg ccttatataa     840
gagacagagt cgtggagcta tatttttgga ttctggtggg agtgtcttat cagcccaaat     900
tcagcactgg tagaattttt ttgtccaaaa taatatgcct tgagaccctc gtagatgata     960
catttgacgc ctacggtact tttgacgagc tcacaatctt tactgaagca gttacaagat    1020
gggacattgg ccacagagat gcactaccag aatacatgaa attcattttc aagacactca    1080
ttgatgtcta tagtgaagct g                                              1101
```

<210> SEQ ID NO 28
<211> LENGTH: 1875
<212> TYPE: DNA
<213> ORGANISM: Clausena lansium

<400> SEQUENCE: 28

```
ctagtagcta aaaaaattat taagttcaat cttttttgtc tgtctagaga aagatgtcaa       60
ctcaacaagt ttcatcagag aacattgttc gtaatgctgc agatttccat cctaatatat      120 ggggaaaacca tttcctcaca tgtctttctc aaacgattga tagttggact caacagcacc     180
acaaagaact gaaagaagag gtgaggaaaa tgatggtgtc tgatgcaaat aaacctgccc     240
agagattgcg cttgattgat actgtccaaa ggttaggtgt ggcttaccac tttgaaaagg     300
agattgatga tgcattggag aaaataggtc atgacccttt tgatgataaa gatgatctct     360
acattgtctc tctttgtttt cgattgctga ggcagcatgg aattaagata tcatgtgatg     420
tgtttgagaa gtttaaagat gacgatggaa aattcaaggc atcattgatg aatgatgttc     480
aaggcatgct aagtttatat gaggcagcac acctagccat tcacggagaa gatattttag     540
atgaagcaat tgttttcacg accactcacc ttaagtcaac ggtatctaat tctcctgtaa     600
actctacttt tgctgaacaa atacgtcatt ctctcagagt tcctctccgt aaagctgtac     660
ctaggttaga gtcgaggtat ttcttggata tctattcaag agatgatttg cacgataaaa     720
ctttgctcaa tttcgcaaag tcagacttta atatactaca agcaatgcac cagaaggaag     780
caagtgagat gaccaggtgg tggagagatt ttgacttcct taaaaagctg ccttatataa     840
gagacagagt cgtggagcta tatttttgga ttctggtggg agtgtcttat cagcccaaat     900
tcagcactgg tagaattttt ttgtccaaaa taatatgcct tgagaccctc gtagatgata     960
catttgacgc ctacggtact tttgacgagc tcacaatctt tactgaagca gttacaagat    1020
gggacattgg ccacagagat gcactaccag aatacatgaa attcattttc aagacactca    1080
ttgatgtcta cagtgaagct gagcaagaac tggcaaagga agggagatca tacagcatac    1140
aatatgcaat acgatcgttc caagaactag ttatgaagta cttctgcgaa gccaagtggt    1200
taaataaagg ttatgttccg agcctggacg attataaatc agtttcatta agaagtatcg    1260
gttttttacc gatagcggta gcttccttcg ttttcatggg tgatattgca actaaggagg    1320
```

-continued

```
tctttgaatg ggaaatgaat aaccctaaga tcataatagc cgcagaaacg attttcagat    1380
tcctggatga catagcaggc cataagtttg agcaaaagag agaacatagt ccatcagcta    1440
ttgaatgcta caagaatcaa catggagtgt ctgaggaaga ggcagttaaa gcgttgtcgt    1500
tagaagttgc taatagttgg aaagatataa atgaggagct gcttctcaac ccaatggcta    1560
ttcctttacc tctgcttcag gtgattcttg atctctcacg ttcggccgat tttatgtacg    1620
gtaatgctca agatcgcttc acgcattcaa cgatgatgaa agaccaagtt gatttggtgc    1680
tgaaggaccc cgttaagctt gacgattaaa gttatgttgc tgatttccta tcgtatattt    1740
gagaagttgg taataaatta agttggtgct tgctagttat ttagctagct agtcatgcgt    1800
agctagggga tggttcaatt gattaggcct atattctagt aaaaataaac gatgtaagaa    1860
caaatctccc tcgca                                                     1875
```

<210> SEQ ID NO 29
<211> LENGTH: 551
<212> TYPE: PRT
<213> ORGANISM: Clausena lansium

<400> SEQUENCE: 29

```
Met Ser Thr Gln Gln Val Ser Ser Glu Asn Ile Val Arg Asn Ala Ala
1               5                   10                  15

Asp Phe His Pro Asn Ile Trp Gly Asn His Phe Leu Thr Cys Leu Ser
            20                  25                  30

Gln Thr Ile Asp Ser Trp Thr Gln Gln His His Lys Glu Leu Lys Glu
        35                  40                  45

Glu Val Arg Lys Met Met Val Ser Asp Ala Asn Lys Pro Ala Gln Arg
    50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110

Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
    130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
                165                 170                 175

Val Ser Asn Ser Pro Val Asn Ser Thr Phe Ala Glu Gln Ile Arg His
            180                 185                 190

Ser Leu Arg Val Pro Leu Arg Lys Ala Val Pro Arg Leu Glu Ser Arg
        195                 200                 205

Tyr Phe Leu Asp Ile Tyr Ser Arg Asp Asp Leu His Asp Lys Thr Leu
    210                 215                 220

Leu Asn Phe Ala Lys Ser Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
            260                 265                 270
```

```
Ile Leu Val Gly Val Ser Tyr Gln Pro Lys Phe Ser Thr Gly Arg Ile
            275                 280                 285

Phe Leu Ser Lys Ile Ile Cys Leu Glu Thr Leu Val Asp Asp Thr Phe
        290                 295                 300

Asp Ala Tyr Gly Thr Phe Asp Glu Leu Thr Ile Phe Thr Glu Ala Val
305                 310                 315                 320

Thr Arg Trp Asp Ile Gly His Arg Asp Ala Leu Pro Glu Tyr Met Lys
                325                 330                 335

Phe Ile Phe Lys Thr Leu Ile Asp Val Tyr Ser Glu Ala Gln Glu
            340                 345                 350

Leu Ala Lys Glu Gly Arg Ser Tyr Ser Ile Gln Tyr Ala Ile Arg Ser
        355                 360                 365

Phe Gln Glu Leu Val Met Lys Tyr Phe Cys Glu Ala Lys Trp Leu Asn
        370                 375                 380

Lys Gly Tyr Val Pro Ser Leu Asp Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
            420                 425                 430

Ile Ile Ile Ala Ala Glu Thr Ile Phe Arg Phe Leu Asp Asp Ile Ala
        435                 440                 445

Gly His Lys Phe Glu Gln Lys Arg Glu His Ser Pro Ser Ala Ile Glu
        450                 455                 460

Cys Tyr Lys Asn Gln His Gly Val Ser Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Gln Val Ile Leu
            500                 505                 510

Asp Leu Ser Arg Ser Ala Asp Phe Met Tyr Gly Asn Ala Gln Asp Arg
            515                 520                 525

Phe Thr His Ser Thr Met Met Lys Asp Gln Val Asp Leu Val Leu Lys
        530                 535                 540

Asp Pro Val Lys Leu Asp Asp
545                 550

<210> SEQ ID NO 30
<211> LENGTH: 1368
<212> TYPE: DNA
<213> ORGANISM: Clausena lansium
<220> FEATURE:
<221> NAME/KEY: misc_feature
<222> LOCATION: (1346)..(1346)
<223> OTHER INFORMATION: n is a, c, g, or t
<220> FEATURE:
<221> NAME/KEY: misc_feature
<222> LOCATION: (1357)..(1357)
<223> OTHER INFORMATION: n is a, c, g, or t
<220> FEATURE:
<221> NAME/KEY: misc_feature
<222> LOCATION: (1362)..(1362)
<223> OTHER INFORMATION: n is a, c, g, or t

<400> SEQUENCE: 30
ttaagtcaat ggtatctaat tctcttgtaa actctacttt tgctgaacaa atacgtcatt      60
ctctcagagt tcctctccat aaagccttac ctaggttaga atcgaggtat ttcttggata     120
tctattcaag agacgatttg cacgataaaa ctttgctcaa tttcgcgaag ttagacttta     180
```

```
atatactaca agtaatgcac cagaaggaag caagtgagat gaccaggtgg tggagagatt    240
ttgacttcct taaaaagctg ccttatataa gagacagagt cgtggagcta tattttttgga   300 ttctggtggg agtgtcttat cagcccaaat tcagcactgg tagaattttt ttgtccaaaa    360
taatatgcct tgagaccctc gtagatgata catttgacgc ctacggtact tttgacgagc    420
tcacaatctt tactgaagca gttacaagat gggacattgg ccacagagat gcactaccag    480
aatacatgaa attcattttc aagacactca ttgatgtcta cagtgaagct gagcaagaac    540
tggcaaagga agggagatca tacagcatac aatatgcaat acggtcgttc caagaactag    600
ttatgaagta cttctgcgaa gccaagtggt taaataaagg ttatgttccg agcctggacg    660
attataaatc agtttcatta agaagtatcg ttttttttacc gatagcggta gcttccttcg    720
ttttcatggg tgatattgca actaaggagg tctttgaatg ggaaatgaat aaccctaaga    780
tcataatagc cgcagaaacg attttcagat tcctggatga catagcaggc cataagtttg    840
agcaaaagag agaacatagt ccatcagcta ttgaatgcta caagaatcaa catggagtgt    900
ctgaggaaga ggcagttaaa gcgttgtcgt tagaagttgc taatagttgg aaagatataa    960
atgaggagct gcttctcaac ccaatggcta ttcctttacc tctgcttcag gtgattcttg   1020
atctctcacg ttcggccgat tttatgtacg gtaatgctca agatcgcttc acgcattcaa   1080
cgatgatgaa agaccaagtt gatttggtgc tgaaggaccc cgttaagctt gacgattaaa   1140
gttatgttgc tgatttccta tcgtatattt gagaagttgg taataaatta agttggtgct   1200
tgctagttat ttagctagct agtcatgcgt agctagggga tggttcaatt gattaggcct   1260
atattctagt aaaaataaac gatgtaagaa caaatctccc tcgcaccaac ttcgcaataa   1320
tgtaatttat ttcatctatg tctatngcag gggtcanaac cnaaaaaa                1368
```

<210> SEQ ID NO 31
<211> LENGTH: 1372
<212> TYPE: DNA
<213> ORGANISM: Clausena lansium
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
<222> LOCATION: (1366)..(1366)
<223> OTHER INFORMATION: n is a, c, g, or t

<400> SEQUENCE: 31

```
ttaagtcaac ggtatctaat tctcctgtaa actctacttt tgccgaacaa atacgtcatt     60
ctctcagagt tcctctccgt aaagctgtac ctaggttaga gtcgaggtat ttcttggata    120
tctattcaag agatgatttg cacgataaaa ctttgctcaa tttcgcaaag ttagactttta   180 atatactaca agcaatgcac cagaaggaag caagtgagat aaccaggtgg tggagagatt    240
ttggattcct tgaaaagctg ccttatgtaa gagacagaat cgtggagata tattttttgga   300 tattggtggg atggtcctat gagccaaaat tcagcactgg tagaatcatt ttgtccaaaa    360
tattatgcct cgtgtccctt gtagatgata catttgacgc ctatggtact cttgaagagc    420
tcacagtctt tactgaagca attacaagat gggacattgg ccacacagat gcactaccag    480
attacatgaa attccttttc aagacactca ttgatgtcta tagtgaagct gaggaagaac    540
tggcaaaggg aggaagatca tacagcatac aatatgcaat acgatcgttt caagaactag    600
ctatgaaata cttctgcgaa gcggagtggt taaataaagg ttatgttccg agcctggacg    660
```

-continued

| | |
|---|---|
| agtataaatc agtttcagta agaagtgtcg gttttttcc gatagcggta gcttccttcg | 720 |
| ttttcatggg tgatattaca actaaggagg tctttgaatg ggaaatgaat aaccctaaga | 780 |
| tcataatagc cgcagaaacg attttcagat tcctggatga tgtggcaggc cataagtttg | 840 |
| agcaaaagag agaacattgt ccatcagcta ttgaatgcta caagaatcaa catggagtgt | 900 |
| ctgaggaaga ggcagttaaa gcgttgtcgt tagaagttgc taatagttgg aaagatataa | 960 |
| atgaggagct gcttctcaac ccaatggcta ttcctttacc tctacttcag gtgattcttg | 1020 |
| atctctcacg ttcggccgat tttatgtacg gcaatggtca agatcgctac acgcattcaa | 1080 |
| cgatgatgaa agaccaagtt gacttggtgc tgaaggaccc cgttaagctt gacgattaaa | 1140 |
| gttatgttgc tgatttccta ttgtatattt gagaagttgg taataaatta agttggtgct | 1200 |
| tgctagttat ttagctagct agtcatgcgt agctaaggga tggttcaatt gattaggcct | 1260 |
| atattctagt aaaaataaaa ggtgtaagaa cgaatctccc tcacaccaac ttcgcaataa | 1320 |
| tgtaatttat ttcatctatg tctgttacaa aaattngaga taaaanaaca gc | 1372 |

<210> SEQ ID NO 32
<211> LENGTH: 31
<212> TYPE: DNA
<213> ORGANISM: Artificial sequence
<220> FEATURE:
<223> OTHER INFORMATION: Primer

<400> SEQUENCE: 32
caccatgtca actcaacaag tttcatcaga g          31

<210> SEQ ID NO 33
<211> LENGTH: 27
<212> TYPE: DNA
<213> ORGANISM: Artificial sequence
<220> FEATURE:
<223> OTHER INFORMATION: Primer

<400> SEQUENCE: 33
actttaatcg tcaagcttaa cggggtc               27

<210> SEQ ID NO 34
<211> LENGTH: 30
<212> TYPE: DNA
<213> ORGANISM: Artificial sequence
<220> FEATURE:
<223> OTHER INFORMATION: Primer

<400> SEQUENCE: 34
ctagccatgg cttcagaaaa agaaattagg            30

<210> SEQ ID NO 35
<211> LENGTH: 40
<212> TYPE: DNA
<213> ORGANISM: Artificial sequence
<220> FEATURE:
<223> OTHER INFORMATION: primer

<400> SEQUENCE: 35
ccggaattcc tatttgcttc tcttgtaaac tttgttcaag          40

<210> SEQ ID NO 36
<211> LENGTH: 42
<212> TYPE: DNA
<213> ORGANISM: Artificial sequence
<220> FEATURE:
<223> OTHER INFORMATION: Primer

<400> SEQUENCE: 36
aaggagatat acatatgaca aaaaaagttg gtgtcggtca gg        42

<210> SEQ ID NO 37
<211> LENGTH: 43
<212> TYPE: DNA
<213> ORGANISM: Artificial sequence
<220> FEATURE:
<223> OTHER INFORMATION: Primer

<400> SEQUENCE: 37
ctttaccaga ctcgagttac gccttttca tctgatcctt tgc        43

<210> SEQ ID NO 38
<211> LENGTH: 1656
<212> TYPE: DNA
<213> ORGANISM: Clausena lansium

<400> SEQUENCE: 38

```
atgtcaactc aacaagtttc atcagagaac attgttcgta acgctgcgaa tttccatcct    60
aatatatggg gaaccatttt cctcacatgt ccttctcaga cgattgatag ttggactcaa   120
cagcaccaca aagaactgaa agaagaggtg aggaaaatga tggtgtctga tgcaaataaa   180
cctgcccaga gattgcgctt gattgatact gtccaaaggt taggtgtggc ttaccacttt   240
gaaaaggaga ttgatgatgc attggagaaa ataggtcatg acccttttga tgataaagat   300
gatctctaca ttgtctctct tgttttcga ttgctgaggc agcatggaat taagatatca   360
tgtgatgtgt ttgagaagtt taaagatgac gatggaaaat tcaaggcatc attgatgaat   420
gatgttcaag gcatgctaag tttatatgag gcagcacacc tagccattca cggagaagat   480
atttagatg aagcaattgt tttcacgacc actcaccta agtcaacggt atctaattct   540
cctgtaaact ctacttttgc tgaacaaata cgtcattctc tcagagttcc tctccgtaaa   600
gctgtaccta ggttagagtc gaggtatttc ttggatatct attcaagaga tgatttgcac   660
gataaaactt tgctcaattt cgcaaagtta gactttaata tactacaagc aatgcaccag   720
aaggaagcaa gtgagatgac caggtggtgg agagattttg acttccttaa aaagctgcct   780
tatataagag acagagtcgt ggagctatat ttttggattc tggtgggagt gtcttatcag   840
cccaaattca gcactggtag aatttttttg tccaaaataa tatgccttga daccctcgta   900
gatgatacat ttgacgccta cggtactttt gacgagctca caatctttac tgaagcagtt   960
acaagatggg acattggcca cagagatgca ctaccagaat acatgaaatt catttttcaag  1020
acactcattg atgtctacag tgaagctgag caagaactgg caaaggaagg gagatcatac  1080
agcatacaat atgcaatacg atcgttccaa gaactagtta tgaagtactt ctgcgaagcc  1140
aagtggttaa ataaaggtta tgttccgagc ctggacgatt ataaatcagt ttcattaaga  1200
agtatcggtt tttaccgat agcggtagct tccttcgttt tcatgggtga tattgcaact  1260
aaggaggtct ttgaatggga atgaataac cctaagatca taatagccgc agaaacgatt  1320
ttcagattcc tggatgacat agcaggccat aagtttgagc aaaagagaga acatagtcca  1380
tcagctattg aatgctacaa gaatcaacat ggagtgtctg aggaagaggc agttaaagcg  1440
ttgtcgttag aagttgctaa tagttggaaa gatataaatg aggagctgct tctcaaccca  1500
atggctattc ctttacctct gcttcaggtg attcttgatc tctcacgttc ggccgatttt  1560
atgtacggta atgctcaaga tcgcctcacg cattcaacga tgatgaaaga ccaagttgat  1620
```

```
ttggtgctga aggaccccgt taagcttgac gattag         1656
```

<210> SEQ ID NO 39
<211> LENGTH: 1656
<212> TYPE: DNA
<213> ORGANISM: Clausena lansium

<400> SEQUENCE: 39

```
atgtcaactc aacaagtttc atcagagaac attgttcgta acgctgcgaa tttccatcct    60
aatatatggg gaaaccattt cctcacatgt ccttctcaga cgattgatag ttggactcaa   120
cagcaccaca aagaactgaa agaagaggtg aggaaaatga tggtgtctga tgcaaataaa   180
cctgcccaga gattgcgctt gattgatact gtccaaaggt taggtgtggc ttaccacttt   240
gaaaaggaga ttgatgatgc attggagaaa ataggtcatg acccttttga tgataaagat   300
gatctctaca ttgtctctct tgttttcga ttgctgaggc agcatggaat taagatatca   360
tgtgatgtgt ttgagaagtt aaagatgac gatggaaaat tcaaggcatc attgatgaat   420
gatgttcaag gcatgctaag tttatatgag gcagcacacc tagccattca cggagaagat   480
attttagatg aagcaattgt tttcacgacc actcaccttc agtcaacggt atctaattct   540
cctgtaaact ctacttttgc tgaacaaata cgtcattctc tcagagttcc tctccgtaaa   600
gctgtaccta ggttagagtc gaggtatttc ttggatatct attcaagaga tgatttgcac   660
gataaaactt tgctcaattt cgcaaagtta gactttaata tactacaagc aatgcaccag   720
aaggaagcaa gtgagatgac caggtggtgg agagattttg acttccttaa aaagctgcct   780
tatataagag acagagtcgt ggagctatat ttttggattc tggtgggagt gtcttatcac   840
cccaaattca gcactggtag aattttttg tccaaaataa tatgccttga ccctcgta    900
gatgatacat ttgacgccta cggtactttt gacgagctca caatctttac tgaagcagtt   960
acaagatggg acattggcca cagagatgca ctaccagaat acatgaaatt catttcaag  1020
acactcattg atgtctacag tgaagctgag caagaactgg caaggaagg gagatcatac  1080
agcatacaat atgcaatacg atcgttccaa gaactagta tgaagtactt ctgcgaagcc  1140
aagtggttaa ataaaggtta tgttccgagc ctggacgatt ataaatcagt tcattaaga  1200
agtatcggtt ttttaccgat agcggtagct tccttcgttt tcatgggtga tattgcaact  1260
aaggaggtct ttgaatggga aatgaataac cctaagatca taatagccgc agaaacgatt  1320
ttcagattcc tggatgacat agcaggccat aagtttgagc aaaagagaga acatagtcca  1380
tcagctattg aatgctacaa gaatcaacat ggagtgtctg aggaagaggc agttaaagcg  1440
ttgtcgttag aagttgctaa tagttggaaa gatataaatg aggagctgct tctcaaccca  1500
atggctattc ctttacctct gcttcaggtg attcttgatc tctcacgttc ggccgatttt  1560
atgtacggta atgctcaaga tcgcctcacg cattcaacga tgatgaaaga ccaagttgat  1620
ttggtgctga aggaccccgt taagcttgac gattag                           1656
```

<210> SEQ ID NO 40
<211> LENGTH: 1656
<212> TYPE: DNA
<213> ORGANISM: Clausena lansium

<400> SEQUENCE: 40

```
atgtcaactc aacaagtttc atcagagaac attgttcgta acgctgcgaa tttccatcct    60
aatatatggg gaaaccattt cctcacatgt ccttctcaga cgattgatag ttggactcaa   120
cagcaccaca aagaactgaa agaagaggtg aggaaaatga tggtgtctga tgcaaataaa   180
```

```
cctgcccaga gattgcgctt gattgatact gtccaaaggc taggtgtggc ttaccacttt    240
gaaaaggaga ttgatgatgc attggagaaa ataggtcatg acccttttga tgataaagat    300
gatctctaca ttgtctctct ttgttttcga ttgctgaggc agcatggaat taagatatca    360
tgtgatgtgt ttgagaagtt taaagatgac gatggaaaat tcaaggcatc attgatgaat    420
gatgttcaag gcatgctaag tttatatgag gcagcacacc tagccattca cggagaagat    480
attttagatg aagcaattgt tttcacgacc actcacctta agtcaacggt atctaattct    540
cctgtaaact ctacttttgc tgaacaaata cgtcattctc tcagagttcc tctccgtaaa    600
gctgtaccta ggtagagtc gaggtatttc ttggatatct attcaagaga tgatttgcac    660
gataaaactt tgctcaattt cgcaaagtta gactttaata tactacaagc aatgcaccag    720
aaggaagcaa gtgagatgac caggtggtgg agagattttg acttccttaa aaagctgcct    780
tatataagag acagagtcgt ggagctatat ttttggattc tggtgggagt gtcttatcag    840
cccaaattca gcactggtag aattttttg tccaaaataa tatgccttga gaccctcgta    900
gatgatacat ttgacgccta cggtactttt gacgagctca caatctttac tgaagcagtt    960
acaagatggg acattggcca cagagatgca ctaccagaat acatgaaatt cattttcaag   1020
acactcattg atgtctacag tgaagctgag caagaactgg caaggaagg gagatcatac   1080
agcatacaat atgcaatacg atcgttccaa gaactagtta tgaagtactt ctgcgaagcc   1140
aagtggttaa ataaaggtta tgttccgagc ctggacgatt ataaatcagt ttcattaaga   1200
agtatcggtt ttttaccgat agcggtagct tccttcgttt tcatgggtga tattgcaact   1260
aaggaggtct ttgaatggga atgaataac cctaagatca taatagccgc agaaacgatt   1320
ttcagattcc tggatgacat agcaggccat aagtttgagc aaaagagaga acatagtcca   1380
tcagctattg aatgctacaa gaatcaacat ggagtgtctg aggaagaggc agttaaagcg   1440
ttgtcgttag aagttgctaa tagttggaaa gatataaatg aggagctgct tctcaaccca   1500
atggctattc ctttacctct gcttcaggtg attcttgatc tctcacgttc ggccgatttt   1560
atgtacggta atgctcaaga tcgcttcacg cattcaacga tgatgaaaga ccaagttgat   1620
ttggtgctga aggaccccgt taagcttgac gattaa                              1656
```

<210> SEQ ID NO 41
<211> LENGTH: 551
<212> TYPE: PRT
<213> ORGANISM: Clausena lansium

<400> SEQUENCE: 41

```
Met Ser Thr Gln Gln Val Ser Ser Glu Asn Ile Val Arg Asn Ala Ala
1               5                   10                  15

Asn Phe His Pro Asn Ile Trp Gly Asn His Phe Leu Thr Cys Pro Ser
            20                  25                  30

Gln Thr Ile Asp Ser Trp Thr Gln Gln His Lys Glu Leu Lys Glu
        35                  40                  45

Glu Val Arg Lys Met Met Val Ser Asp Ala Asn Lys Pro Ala Gln Arg
    50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110
```

-continued

```
Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
                165                 170                 175

Val Ser Asn Ser Pro Val Asn Ser Thr Phe Ala Glu Gln Ile Arg His
                180                 185                 190

Ser Leu Arg Val Pro Leu Arg Lys Ala Val Pro Arg Leu Glu Ser Arg
        195                 200                 205

Tyr Phe Leu Asp Ile Tyr Ser Arg Asp Asp Leu His Asp Lys Thr Leu
        210                 215                 220

Leu Asn Phe Ala Lys Leu Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
                260                 265                 270

Ile Leu Val Gly Val Ser Tyr Gln Pro Lys Phe Ser Thr Gly Arg Ile
        275                 280                 285

Phe Leu Ser Lys Ile Ile Cys Leu Glu Thr Leu Val Asp Asp Thr Phe
        290                 295                 300

Asp Ala Tyr Gly Thr Phe Asp Glu Leu Thr Ile Phe Thr Glu Ala Val
305                 310                 315                 320

Thr Arg Trp Asp Ile Gly His Arg Asp Ala Leu Pro Glu Tyr Met Lys
                325                 330                 335

Phe Ile Phe Lys Thr Leu Ile Asp Val Tyr Ser Glu Ala Glu Gln Glu
                340                 345                 350

Leu Ala Lys Glu Gly Arg Ser Tyr Ser Ile Gln Tyr Ala Ile Arg Ser
        355                 360                 365

Phe Gln Glu Leu Val Met Lys Tyr Phe Cys Glu Ala Lys Trp Leu Asn
        370                 375                 380

Lys Gly Tyr Val Pro Ser Leu Asp Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
                420                 425                 430

Ile Ile Ile Ala Ala Glu Thr Ile Phe Arg Phe Leu Asp Asp Ile Ala
        435                 440                 445

Gly His Lys Phe Glu Gln Lys Arg Glu His Ser Pro Ser Ala Ile Glu
        450                 455                 460

Cys Tyr Lys Asn Gln His Gly Val Ser Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Leu Gln Val Ile Leu
                500                 505                 510

Asp Leu Ser Arg Ser Ala Asp Phe Met Tyr Gly Asn Ala Gln Asp Arg
        515                 520                 525
```

Leu Thr His Ser Thr Met Met Lys Asp Gln Val Asp Leu Val Leu Lys
    530                 535                 540

Asp Pro Val Lys Leu Asp Asp
545                 550

<210> SEQ ID NO 42
<211> LENGTH: 551
<212> TYPE: PRT
<213> ORGANISM: Clausena lansium

<400> SEQUENCE: 42

Met Ser Thr Gln Gln Val Ser Ser Glu Asn Ile Val Arg Asn Ala Ala
1               5                   10                  15

Asn Phe His Pro Asn Ile Trp Gly Asn His Phe Leu Thr Cys Pro Ser
            20                  25                  30

Gln Thr Ile Asp Ser Trp Thr Gln Gln His His Lys Glu Leu Lys Glu
        35                  40                  45

Glu Val Arg Lys Met Met Val Ser Asp Ala Asn Lys Pro Ala Gln Arg
    50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110

Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
    130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
                165                 170                 175

Val Ser Asn Ser Pro Val Asn Ser Thr Phe Ala Glu Gln Ile Arg His
            180                 185                 190

Ser Leu Arg Val Pro Leu Arg Lys Ala Val Pro Arg Leu Glu Ser Arg
        195                 200                 205

Tyr Phe Leu Asp Ile Tyr Ser Arg Asp Asp Leu His Asp Lys Thr Leu
    210                 215                 220

Leu Asn Phe Ala Lys Leu Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
            260                 265                 270

Ile Leu Val Gly Val Ser Tyr His Pro Lys Phe Ser Thr Gly Arg Ile
        275                 280                 285

Phe Leu Ser Lys Ile Ile Cys Leu Glu Thr Leu Val Asp Asp Thr Phe
    290                 295                 300

Asp Ala Tyr Gly Thr Phe Asp Glu Leu Thr Ile Phe Thr Glu Ala Val
305                 310                 315                 320

Thr Arg Trp Asp Ile Gly His Arg Asp Ala Leu Pro Glu Tyr Met Lys
                325                 330                 335

Phe Ile Phe Lys Thr Leu Ile Asp Val Tyr Ser Glu Ala Glu Gln Glu
            340                 345                 350

```
Leu Ala Lys Glu Gly Arg Ser Tyr Ser Ile Gln Tyr Ala Ile Arg Ser
            355                 360                 365

Phe Gln Glu Leu Val Met Lys Tyr Phe Cys Glu Ala Lys Trp Leu Asn
        370                 375                 380

Lys Gly Tyr Val Pro Ser Leu Asp Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
            420                 425                 430

Ile Ile Ile Ala Ala Glu Thr Ile Phe Arg Phe Leu Asp Asp Ile Ala
                435                 440                 445

Gly His Lys Phe Glu Gln Lys Arg Glu His Ser Pro Ser Ala Ile Glu
        450                 455                 460

Cys Tyr Lys Asn Gln His Gly Val Ser Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Leu Gln Val Ile Leu
            500                 505                 510

Asp Leu Ser Arg Ser Ala Asp Phe Met Tyr Gly Asn Ala Gln Asp Arg
        515                 520                 525

Leu Thr His Ser Thr Met Met Lys Asp Gln Val Asp Leu Val Leu Lys
        530                 535                 540

Asp Pro Val Lys Leu Asp Asp
545                 550

<210> SEQ ID NO 43
<211> LENGTH: 551
<212> TYPE: PRT
<213> ORGANISM: Clausena lansium

<400> SEQUENCE: 43

Met Ser Thr Gln Gln Val Ser Ser Glu Asn Ile Val Arg Asn Ala Ala
1               5                   10                  15

Asn Phe His Pro Asn Ile Trp Gly Asn His Phe Leu Thr Cys Pro Ser
            20                  25                  30

Gln Thr Ile Asp Ser Trp Thr Gln Gln His His Lys Glu Leu Lys Glu
        35                  40                  45

Glu Val Arg Lys Met Met Val Ser Asp Ala Asn Lys Pro Ala Gln Arg
    50                  55                  60

Leu Arg Leu Ile Asp Thr Val Gln Arg Leu Gly Val Ala Tyr His Phe
65                  70                  75                  80

Glu Lys Glu Ile Asp Asp Ala Leu Glu Lys Ile Gly His Asp Pro Phe
                85                  90                  95

Asp Asp Lys Asp Asp Leu Tyr Ile Val Ser Leu Cys Phe Arg Leu Leu
            100                 105                 110

Arg Gln His Gly Ile Lys Ile Ser Cys Asp Val Phe Glu Lys Phe Lys
        115                 120                 125

Asp Asp Asp Gly Lys Phe Lys Ala Ser Leu Met Asn Asp Val Gln Gly
    130                 135                 140

Met Leu Ser Leu Tyr Glu Ala Ala His Leu Ala Ile His Gly Glu Asp
145                 150                 155                 160

Ile Leu Asp Glu Ala Ile Val Phe Thr Thr Thr His Leu Lys Ser Thr
```

```
                165                 170                 175
Val Ser Asn Ser Pro Val Asn Ser Thr Phe Ala Glu Gln Ile Arg His
            180                 185                 190

Ser Leu Arg Val Pro Leu Arg Lys Ala Val Pro Arg Leu Glu Ser Arg
            195                 200                 205

Tyr Phe Leu Asp Ile Tyr Ser Arg Asp Leu His Asp Lys Thr Leu
    210                 215                 220

Leu Asn Phe Ala Lys Leu Asp Phe Asn Ile Leu Gln Ala Met His Gln
225                 230                 235                 240

Lys Glu Ala Ser Glu Met Thr Arg Trp Trp Arg Asp Phe Asp Phe Leu
                245                 250                 255

Lys Lys Leu Pro Tyr Ile Arg Asp Arg Val Val Glu Leu Tyr Phe Trp
                260                 265                 270

Ile Leu Val Gly Val Ser Tyr Gln Pro Lys Phe Ser Thr Gly Arg Ile
            275                 280                 285

Phe Leu Ser Lys Ile Ile Cys Leu Glu Thr Leu Val Asp Asp Thr Phe
    290                 295                 300

Asp Ala Tyr Gly Thr Phe Asp Glu Leu Thr Ile Phe Thr Glu Ala Val
305                 310                 315                 320

Thr Arg Trp Asp Ile Gly His Arg Asp Ala Leu Pro Glu Tyr Met Lys
                325                 330                 335

Phe Ile Phe Lys Thr Leu Ile Asp Val Tyr Ser Glu Ala Glu Gln Glu
                340                 345                 350

Leu Ala Lys Glu Gly Arg Ser Tyr Ser Ile Gln Tyr Ala Ile Arg Ser
            355                 360                 365

Phe Gln Glu Leu Val Met Lys Tyr Phe Cys Glu Ala Lys Trp Leu Asn
    370                 375                 380

Lys Gly Tyr Val Pro Ser Leu Asp Tyr Lys Ser Val Ser Leu Arg
385                 390                 395                 400

Ser Ile Gly Phe Leu Pro Ile Ala Val Ala Ser Phe Val Phe Met Gly
                405                 410                 415

Asp Ile Ala Thr Lys Glu Val Phe Glu Trp Glu Met Asn Asn Pro Lys
                420                 425                 430

Ile Ile Ile Ala Ala Glu Thr Ile Phe Arg Phe Leu Asp Asp Ile Ala
            435                 440                 445

Gly His Lys Phe Glu Gln Lys Arg Glu His Ser Pro Ser Ala Ile Glu
    450                 455                 460

Cys Tyr Lys Asn Gln His Gly Val Ser Glu Glu Ala Val Lys Ala
465                 470                 475                 480

Leu Ser Leu Glu Val Ala Asn Ser Trp Lys Asp Ile Asn Glu Glu Leu
                485                 490                 495

Leu Leu Asn Pro Met Ala Ile Pro Leu Pro Leu Leu Gln Val Ile Leu
                500                 505                 510

Asp Leu Ser Arg Ser Ala Asp Phe Met Tyr Gly Asn Ala Gln Asp Arg
            515                 520                 525

Phe Thr His Ser Thr Met Met Lys Asp Gln Val Asp Leu Val Leu Lys
    530                 535                 540

Asp Pro Val Lys Leu Asp Asp
545                 550

<210> SEQ ID NO 44
<211> LENGTH: 70
<212> TYPE: PRT
<213> ORGANISM: Clausena lansium
```

<400> SEQUENCE: 44

Ala Ala Glu Thr Ile Phe Arg Phe Leu Asp Asp Val Ala Gly His Lys
1               5                   10                  15

Phe Glu Gln Lys Arg Glu His Cys Pro Ser Ala Ile Glu Cys Tyr Lys
            20                  25                  30

Asn Gln His Gly Val Ser Glu Glu Ala Val Lys Ala Leu Ser Leu
        35                  40                  45

Glu Val Ala Asn Ser Trp Lys Asp Ile Asn Glu Leu Leu Leu Asn
    50                  55                  60

Pro Met Ala Ile Pro Leu
65                  70

<210> SEQ ID NO 45
<211> LENGTH: 145
<212> TYPE: PRT
<213> ORGANISM: Clausena lansium

<400> SEQUENCE: 45

Ser Lys Ile Ile Cys Leu Glu Thr Leu Val Asp Asp Thr Phe Asp Ala
1               5                   10                  15

Tyr Gly Thr Phe Glu Glu Leu Thr Ile Phe Thr Glu Ala Val Thr Arg
            20                  25                  30

Trp Asp Ile Gly His Thr Asp Ala Leu Pro Asp Tyr Met Lys Phe Leu
        35                  40                  45

Phe Lys Thr Leu Ile Asp Val Tyr Ser Glu Ala Glu Glu Leu Ala
    50                  55                  60

Lys Glu Gly Arg Ser Tyr Ser Ile Gln Tyr Ala Ile Arg Ser Phe Gln
65                  70                  75                  80

Glu Leu Ala Met Lys Tyr Phe Cys Glu Ala Lys Trp Leu Asn Lys Gly
                85                  90                  95

Tyr Val Pro Ser Leu Asp Asp Tyr Lys Ser Val Ser Leu Arg Ser Ile
            100                 105                 110

Gly Phe Leu Pro Ile Ala Val Ala Ser Phe Val Phe Met Gly Asp Ile
        115                 120                 125

Ala Thr Lys Glu Val Phe Glu Trp Glu Met Asn Asn Pro Lys Ile Ile
    130                 135                 140

Ile
145

<210> SEQ ID NO 46
<211> LENGTH: 23
<212> TYPE: PRT
<213> ORGANISM: Clausena lansium

<400> SEQUENCE: 46

Arg Ser Ala Asp Phe Met Tyr Gly Asn Gly Gln Asp Arg Tyr Thr His
1 5 10 15

Ser Thr Met Met Lys Asp Gln
20

<210> SEQ ID NO 47
<211> LENGTH: 44
<212> TYPE: PRT
<213> ORGANISM: Clausena lansium

<400> SEQUENCE: 47

Asp Pro Phe Asp Asp Lys Asp Asp Leu Tyr Ile Val Ser Leu Cys Phe

-continued

```
                1               5                  10                  15
            Arg Leu Leu Arg Gln His Gly Ile Lys Ile Ser Cys Asp Val Phe Glu
                            20                  25                  30
            Lys Phe Lys Asp Asp Asp Gly Lys Phe Lys Ala Ser
                        35                  40

<210> SEQ ID NO 48
<211> LENGTH: 57
<212> TYPE: PRT
<213> ORGANISM: Clausena lansium

<400> SEQUENCE: 48

Glu Ser Arg Tyr Phe Leu Asp Ile Tyr Ser Arg Asp Asp Leu His Asp
1               5                   10                  15

Lys Thr Leu Leu Asn Phe Ala Lys Leu Asp Phe Asn Ile Leu Gln Ala
            20                  25                  30

Met His Gln Lys Glu Ala Ser Glu Ile Thr Arg Trp Trp Arg Asp Phe
        35                  40                  45

Gly Phe Leu Glu Lys Leu Pro Tyr Val
    50                  55

<210> SEQ ID NO 49
<211> LENGTH: 24
<212> TYPE: PRT
<213> ORGANISM: Clausena lansium

<400> SEQUENCE: 49

Leu Met Asp Asp Ile Val Ser His Lys Phe Glu Gln Ser Arg Gly His
1               5                   10                  15

Val Ala Ser Ser Val Glu Cys Tyr
            20

<210> SEQ ID NO 50
<211> LENGTH: 15
<212> TYPE: PRT
<213> ORGANISM: Clausena lansium

<400> SEQUENCE: 50

Thr Ala Phe Pro Val Ala Leu Ile Glu Arg Pro Phe Asn Ile Ala
1               5                   10                  15

<210> SEQ ID NO 51
<211> LENGTH: 12
<212> TYPE: PRT
<213> ORGANISM: Clausena lansium

<400> SEQUENCE: 51

Leu Asp Glu Ala Ile Val Phe Thr Thr Thr His Leu
1               5                   10

<210> SEQ ID NO 52
<211> LENGTH: 12
<212> TYPE: PRT
<213> ORGANISM: Clausena lansium

<400> SEQUENCE: 52

Lys Tyr Glu Asp Gly Tyr Thr His Ser Ala Val Val
1               5                   10

<210> SEQ ID NO 53
<211> LENGTH: 15
<212> TYPE: PRT
```

-continued

<213> ORGANISM: Clausena lansium

<400> SEQUENCE: 53

Leu Leu Met Arg Ile Leu Asn Leu Thr Arg Val Ile Asp Val Ile
1               5                   10                  15

<210> SEQ ID NO 54
<211> LENGTH: 14
<212> TYPE: PRT
<213> ORGANISM: Clausena lansium

<400> SEQUENCE: 54

Gln Lys Glu Leu Gly Asp Ile Ser Arg Trp Trp Lys Glu Leu
1               5                   10

<210> SEQ ID NO 55
<211> LENGTH: 14
<212> TYPE: PRT
<213> ORGANISM: Clausena lansium

<400> SEQUENCE: 55

Ala Trp Asn Glu Phe Arg Lys Gln Val Ser Asn Ala Trp Lys
1               5                   10

<210> SEQ ID NO 56
<211> LENGTH: 10
<212> TYPE: PRT
<213> ORGANISM: Clausena lansium

<400> SEQUENCE: 56

Thr Pro Phe Val Gly Met Gly Asp Ile Val
1               5                   10

<210> SEQ ID NO 57
<211> LENGTH: 12
<212> TYPE: PRT
<213> ORGANISM: Clausena lansium

<400> SEQUENCE: 57

Asn Arg Ala Glu Gln Ile Asn His Ala Leu Asp Cys
1               5                   10

<210> SEQ ID NO 58
<211> LENGTH: 11
<212> TYPE: PRT
<213> ORGANISM: Clausena lansium

<400> SEQUENCE: 58

Trp Lys Asp Ile Asn Glu Glu Cys Leu Arg Pro
1               5                   10

<210> SEQ ID NO 59
<211> LENGTH: 9
<212> TYPE: PRT
<213> ORGANISM: Clausena lansium

<400> SEQUENCE: 59

Gly His Val Ala Ser Ser Val Glu Cys
1               5

<210> SEQ ID NO 60
<211> LENGTH: 10
<212> TYPE: PRT
<213> ORGANISM: Clausena lansium -continued

<400> SEQUENCE: 60

Arg Leu Leu Arg Gln Gln Gly Phe Lys Val
1               5                   10

<210> SEQ ID NO 61
<211> LENGTH: 560
<212> TYPE: PRT
<213> ORGANISM: Clausena lansium

<400> SEQUENCE: 61

Met Lys Asp Met Ser Ile Pro Leu Leu Ala Ala Val Ser Ser Ser Thr
1               5                   10                  15

Glu Glu Thr Val Arg Pro Ile Ala Asp Phe His Pro Thr Leu Trp Gly
                20                  25                  30

Asn His Phe Leu Lys Ser Ala Ala Asp Val Glu Thr Ile Asp Ala Ala
            35                  40                  45

Thr Gln Glu Gln His Ala Ala Leu Lys Gln Glu Val Arg Arg Met Ile
        50                  55                  60

Thr Thr Thr Ala Asn Lys Leu Ala Gln Lys Leu His Met Ile Asp Ala
65                  70                  75                  80

Val Gln Arg Leu Gly Val Ala Tyr His Phe Glu Lys Glu Ile Glu Asp
                85                  90                  95

Glu Leu Gly Lys Val Ser His Asp Leu Asp Ser Asp Asp Leu Tyr Val
                100                 105                 110

Val Ser Leu Arg Phe Arg Leu Phe Arg Gln Gln Gly Val Lys Ile Ser
            115                 120                 125

Cys Asp Val Phe Asp Lys Phe Lys Asp Glu Gly Lys Phe Lys Glu
        130                 135                 140

Ser Leu Ile Asn Asp Ile Arg Gly Met Leu Ser Leu Tyr Glu Ala Ala
145                 150                 155                 160

Tyr Leu Ala Ile Arg Gly Glu Asp Ile Leu Asp Glu Ala Ile Val Phe
                165                 170                 175

Thr Thr Thr His Leu Lys Ser Val Ile Ser Ile Ser Asp His Ser His
            180                 185                 190

Ala Asn Ser Asn Leu Ala Glu Gln Ile Arg His Ser Leu Gln Ile Pro
        195                 200                 205

Leu Arg Lys Ala Ala Ala Arg Leu Glu Ala Arg Tyr Phe Leu Asp Ile
    210                 215                 220

Tyr Ser Arg Asp Asp Leu His Asp Glu Thr Leu Leu Lys Phe Ala Lys
225                 230                 235                 240

Leu Asp Phe Asn Ile Leu Gln Ala Ala His Gln Lys Glu Ala Ser Ile
                245                 250                 255

Met Thr Arg Trp Trp Asn Asp Leu Gly Phe Pro Lys Lys Val Pro Tyr
                260                 265                 270

Ala Arg Asp Arg Ile Ile Glu Thr Tyr Ile Trp Met Leu Leu Gly Val
            275                 280                 285

Ser Tyr Glu Pro Asn Leu Ala Phe Gly Arg Ile Phe Ala Ser Lys Val
        290                 295                 300

Val Cys Met Ile Thr Thr Ile Asp Asp Thr Phe Asp Ala Tyr Gly Thr
305                 310                 315                 320

Phe Glu Glu Leu Thr Leu Phe Thr Glu Ala Val Thr Arg Trp Asp Ile
                325                 330                 335

Gly Leu Ile Asp Thr Leu Pro Glu Tyr Met Lys Phe Ile Val Lys Ala
            340                 345                 350

| | | | | | | | | | | | | |
|---|---|---|---|---|---|---|---|---|---|---|---|---|
| Leu | Leu | Asp<br>355 | Ile | Tyr | Arg | Glu<br>360 | Ala | Glu | Glu | Leu<br>365 | Ala | Lys | Glu | Gly |
| Arg | Ser<br>370 | Tyr | Gly | Ile | Pro<br>375 | Tyr | Ala | Lys | Gln<br>380 | Met | Met | Gln | Glu | Leu | Ile |
| Ile<br>385 | Leu | Tyr | Phe | Thr<br>390 | Glu | Ala | Lys | Trp | Leu<br>395 | Tyr | Lys | Gly | Tyr | Val | Pro<br>400 |
| Thr | Phe | Asp | Glu | Tyr<br>405 | Lys | Ser | Val | Ala | Leu<br>410 | Arg | Ser | Ile | Gly<br>415 | Leu | Arg |
| Thr | Leu | Ala | Val<br>420 | Ala | Ser | Phe | Val<br>425 | Asp | Leu | Gly | Asp | Phe<br>430 | Ile | Ala | Thr |
| Lys | Asp | Asn<br>435 | Phe | Glu | Cys | Ile<br>440 | Leu | Lys | Asn | Ala | Lys<br>445 | Ser | Leu | Lys | Ala |
| Thr | Glu<br>450 | Thr | Ile | Gly | Arg<br>455 | Leu | Met | Asp | Asp | Ile<br>460 | Ala | Gly | Tyr | Lys | Phe |
| Glu<br>465 | Gln | Lys | Arg | Gly | His<br>470 | Asn | Pro | Ser | Ala | Val<br>475 | Glu | Cys | Tyr | Lys | Asn<br>480 |
| Gln | His | Gly | Val | Ser<br>485 | Glu | Glu | Glu | Ala | Val<br>490 | Lys | Glu | Leu | Leu<br>495 | Leu | Glu |
| Val | Ala | Asn | Ser<br>500 | Trp | Lys | Asp | Ile | Asn<br>505 | Glu | Glu | Leu | Leu | Asn<br>510 | Pro | Thr |
| Thr | Val | Pro<br>515 | Leu | Pro | Met | Leu | Gln<br>520 | Arg | Leu | Leu | Tyr | Phe<br>525 | Ala | Arg | Ser |
| Gly | His<br>530 | Phe | Ile | Tyr | Asp<br>535 | Asp | Gly | His | Asp | Arg<br>540 | Tyr | Thr | His | Ser | Leu |
| Met<br>545 | Met | Lys | Arg | Gln | Val<br>550 | Ala | Leu | Leu | Leu | Thr<br>555 | Glu | Pro | Leu | Ala | Ile<br>560 |

What is claimed is:

1. A method for producing isolated α-santalene comprising:
a) contacting FPP with at least one polypeptide having an α-santalene synthase activity and comprising an amino acid sequence at least 90% identical to SEQ ID NO: 1; and
b) recovering the α-santalene produced in step a).

2. A method for producing α-santalene comprising:
a) contacting FPP with at least one polypeptide having an α-santalene synthase activity and comprising an amino acid sequence at least 90% identical to SEQ ID NO: 1, wherein step a) comprises cultivating a non-human host organism or cell capable of producing FPP and transformed to express at least one polypeptide comprising an amino acid sequence at least 90% identical to SEQ ID NO: 1 and having an α-santalene synthase activity, under conditions conducive to the production of α-santalene; and
b) optionally, recovering the α-santalene produced in step a).

3. The method of claim 2, wherein the method further comprises, prior to step a), transforming a non human host organism or cell capable of producing FPP with at least one nucleic acid encoding a polypeptide comprising an amino acid sequence at least 90% identical to SEQ ID NO: 1 and having an α-santalene synthase activity, so that said organism expresses said polypeptide.

4. The method of claim 3, wherein the at least one nucleic acid encoding the α-santalene synthase comprises the nucleotide sequence of SEQ ID NO: 2 or the complement thereof.

5. The method of claim 2, wherein the non-human host organism is a plant, a prokaryote, or a fungus and wherein the non-human host cell is a plant or a fungal cell.

6. A method for producing isolated α-santalene or a mixture of sesquiterpenes comprising:
a) contacting FPP with at least one polypeptide having an α-santalene synthase activity and comprising an amino acid sequence at least 90% identical to SEQ ID NO: 1, wherein α-santalene or (+)-α-santalene is the major product or in which α-santalene or (+)-α-santalene represents at least 60%, at least 80%, or at least 90%, of the sesquiterpenes obtained; and
b) optionally, recovering the α-santalene or mixture of sesquiterpenes produced in step a).

7. The method of claim 1, wherein the at least one polypeptide comprises an amino acid sequence at least 95% identical to SEQ ID NO: 1, the amino acid sequence SEQ ID NO: 1 or an amino acid sequence obtained by modifying SEQ ID NO: 1.

8. A cDNA encoding a polypeptide having an α-santalene synthase activity and comprising an amino acid sequence at least 90% identical to SEQ ID NO: 1.

9. The cDNA of claim 8, comprising the nucleotide sequence of SEQ ID NO: 2 or the complement thereof.

10. An expression vector comprising the nucleic acid of claim 8, in the form of a viral vector, a bacteriophage or a plasmid.

11. The expression vector of claim 10, including the nucleic acid operably linked to at least one regulatory sequence which controls transcription, translation initiation or termination, and, optionally, including at least one selection marker.

12. A non-human host organism or cell transformed to harbor at least one nucleic acid according to claim 8, so that it heterologously expresses or over-expresses at least one polypeptide having an α-santalene synthase activity or a (+)-α-synthase activity and comprising an amino acid sequence at least 90% identical to SEQ ID NO: 1.

13. The non-human host organism or cell of claim 12, wherein the non-human host organism is a plant, a prokaryote, or a fungus and wherein the non-human host cell is a plant or a fungal cell.

14. A method for producing at least one polypeptide having an α-santalene synthase activity comprising:
   a) culturing a non-human host organism or cell transformed with an expression vector comprising a nucleic acid encoding a polypeptide having an α-santalene synthase activity or a (+)-α-santalene synthase activity and comprising an amino acid sequence at least 90% identical to SEQ ID NO: 1, so that it harbors said nucleic acid and expresses or overexpresses said polypeptide; and
   b) isolating the polypeptide from the non-human host organism or cell cultured in step a);
   wherein the polypeptide having an α-santalene synthase activity comprises an amino acid sequence having at least 90%, 95%, or 100% sequence identity to SEQ ID NO: 1.

15. The method of claim 14, further comprising, prior to step a), transforming a non-human host organism or cell with the expression vector, so that it harbors the nucleic acid and expresses or over-expresses the polypeptide.

16. A method for preparing a variant polypeptide having an α-santalene synthase activity comprising the steps of:
   (a) selecting a nucleic acid according to claim 8;
   (b) modifying the selected nucleic acid to obtain at least one mutant nucleic acid;
   (c) transforming host cells or unicellular organisms with the mutant nucleic acid sequence to express a polypeptide encoded by the mutant nucleic acid sequence;
   (d) screening the polypeptide for at least one modified property; and,
   (e) optionally, if the polypeptide has no desired variant α-santalene synthase activity, repeating the process steps (a) to (d) until a polypeptide with a desired variant α-santalene synthase activity is obtained;
   (f) optionally, if a polypeptide having a desired variant α-santalene synthase activity was identified in step d), isolating the corresponding mutant nucleic acid obtained in step (c).

17. A method according to claim 16, wherein the variant polypeptide prepared is capable of producing a mixture of sesquiterpenes wherein α-santalene or (+)-α-santalene is the major product or in which α-santalene or (+)-α-santalene represents at least 60%, at least 80%, or at least 90%, of the sesquiterpenes obtained.

18. The non-human host organism or cell of claim 12 wherein the non-human host organism is a microorganism.

19. The non-human host organism or cell of claim 12 wherein the microorganism is a bacteria or yeast.

20. The non-human host organism or cell of claim 12 wherein bacteria is *E. coli* or the yeast is *Saccharomyces cerevisiae*.

21. The method of claim 2, further comprising processing the α-santalene to a α-santalene derivative using a chemical or biochemical synthesis or a combination of both.

22. The method of claim 21, wherein the derivative comprises a α-santalol.

* * * * *